United States Patent
Cockerill

(10) Patent No.: US 11,247,973 B2
(45) Date of Patent: Feb. 15, 2022

(54) ANTIVIRAL BENZODIAZEPINE COMPOUNDS

(71) Applicant: The University of Durham, Durham (GB)

(72) Inventor: Stuart Cockerill, Durham (GB)

(73) Assignee: The University of Durham, Durham (GB)

( * ) Notice: Subject to any disclaimer, the term of this patent is extended or adjusted under 35 U.S.C. 154(b) by 0 days.

(21) Appl. No.: 16/323,496

(22) PCT Filed: Aug. 15, 2017

(86) PCT No.: PCT/GB2017/052393
§ 371 (c)(1),
(2) Date: Feb. 5, 2019

(87) PCT Pub. No.: WO2018/033714
PCT Pub. Date: Feb. 22, 2018

(65) Prior Publication Data
US 2021/0017138 A1    Jan. 21, 2021

(30) Foreign Application Priority Data

Aug. 15, 2016 (GB) .................... 1613942

(51) Int. Cl.
*C07D 243/24* (2006.01)
*A61P 31/14* (2006.01)
(Continued)

(52) U.S. Cl.
CPC ............ *C07D 243/24* (2013.01); *A61P 31/14* (2018.01); *C07D 243/26* (2013.01);
(Continued)

(58) Field of Classification Search
CPC .. C07D 243/24; C07D 243/26; C07D 401/12; C07D 401/14; C07D 403/12; A61P 31/14
See application file for complete search history.

(56) References Cited

U.S. PATENT DOCUMENTS 5,004,741 A * 4/1991 Evans ................... C07C 271/22
                                                        514/221
5,817,658 A    10/1998 Siegl et al.
(Continued)

FOREIGN PATENT DOCUMENTS

EP          0284256      9/1988
WO    WO-2000012547 A2 *   3/2000 ............. C07K 14/02
(Continued)

OTHER PUBLICATIONS

Carter; Annual Reports in Medicinal Chemistry, 2008, 43, 229-245. (Year: 2008).*
(Continued)

*Primary Examiner* — Daniel R Carcanague
(74) *Attorney, Agent, or Firm* — Rudy J. Ng; Bozicevic, Field & Francis LLP

(57) ABSTRACT

The invention relates to compounds of formula (I), and pharmaceutical uses thereof. Particular aspects of the invention relate to methods of synthesising the compounds and the use of those compounds in treating, ameliorating, or preventing a microbial infection.

21 Claims, 1 Drawing Sheet

(51) Int. Cl.
  C07D 243/26 (2006.01)
  C07D 401/12 (2006.01)
  C07D 401/14 (2006.01)
  C07D 403/12 (2006.01)
(52) U.S. Cl.
  CPC ......... C07D 401/12 (2013.01); C07D 401/14 (2013.01); C07D 403/12 (2013.01)

(56) References Cited

U.S. PATENT DOCUMENTS

| | | | | |
|---|---|---|---|---|
| 8,039,616 B2* | 10/2011 | Dennison | ............ | A61P 31/14 540/504 |
| 8,119,630 B2* | 2/2012 | Carter | ............ | A61P 29/00 514/221 |
| 10,406,166 B2* | 9/2019 | Cockerill | ............ | C07D 401/04 |
| 2007/0185096 A1* | 8/2007 | Powell | ............ | A61K 45/06 514/221 |
| 2008/0139536 A1* | 6/2008 | Dowdell | ............ | C07D 405/12 514/221 |
| 2017/0022221 A1* | 1/2017 | Shook | ............ | C07D 513/04 |
| 2018/0085378 A1* | 3/2018 | Cockerill | ............ | A61P 31/00 |

FOREIGN PATENT DOCUMENTS

| | | | | |
|---|---|---|---|---|
| WO | 2004026843 | 1/2004 | | |
| WO | 2005089769 | 9/2005 | | |
| WO | 2005089770 | 9/2005 | | |
| WO | 2005089771 | 9/2005 | | |
| WO | 2005090319 | 9/2005 | | |
| WO | 2008063634 | 5/2008 | | |
| WO | WO-2011151651 A1 * | 12/2011 | ............ | C07D 401/12 |
| WO | WO-2011151652 A1 * | 12/2011 | ............ | C07D 243/26 |
| WO | WO-2016166546 A1 * | 10/2016 | ............ | C07D 401/04 |
| WO | WO2021032992 | * | 2/2021 | |

OTHER PUBLICATIONS

Chapman; Antimicrobial Agents and Chemotherapy Aug. 2007, 51, 3346-3353. (Year: 2007).*
Glenn; Journal of Virology Nov. 1998, 72 (11) 9303-9306. (Year: 1998).*
Barr; Ther Adv Infect Dis. 2019, 6, 1-9. doi:10.1177/2049936119865798 (Year: 2019).*
Evans; J. Med. Chem. 1988, 31, 12, 2235-2246. (Year: 1988).*
Henderson; Journal of Medicinal Chemistry 2007, 50, 7, 1685-1692. (Year: 2007).*
Database Registry (2009) Accession No. 1027408-86-1, 1.
Tokarski J S et al "Three-Dimensional Molecular Shape Analysis-Quantitative Structure-Activity Relationship of A Series Of Cholecystokinin-A Receptor Antagonists" Journal of Medicinal Chemistry, American Chemical Society, vol. 37, No. 21, (Oct. 14, 1994), 3639-3654.

* cited by examiner

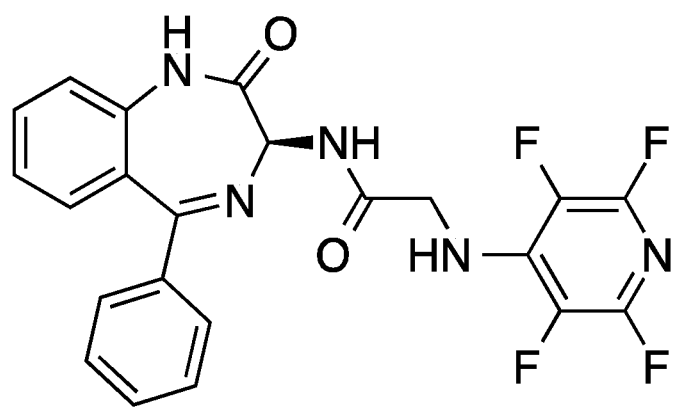

ANTIVIRAL BENZODIAZEPINE COMPOUNDS

CROSS-REFERENCE TO RELATED APPLICATIONS

This application is the U.S. national phase under 35 U.S.C. § 371 of PCT International Application No. PCT/GB2017/052393, which has an international filing date of Aug. 15, 2017 and designated the United States of America, which application claims benefit of priority to GB Application No. 1613942.0, filed Aug. 15, 2016, the disclosures of each of which are incorporated by reference herein.

The present invention relates to antimicrobial compounds for use in treating microbial infections. The invention extends to the compounds per se, pharmaceutical compositions, methods of making the compounds and methods of treating microbial infections.

Over the last forty years, fluorine-containing compounds have played a key role in the development of new pharmaceuticals, crop protection agents and insecticides[2,3] where a significant number of these products contain one or more fluorine atoms[1]. The interest in the use of fluorine as a design component in medicinal chemistry has been largely due to its ability to affect the physicochemical and biological properties of compounds where it is incorporated. The low steric impact of the small van der Waals ratio coupled with its high electronegativity, the ability to participate in hydrogen bonding and the inherent carbon-fluorine bond stability to metabolic transformation are well known features. In addition, there are many examples of the incorporation of the fluorine atom and the range of effect of this substituent on lipophilicity[4]. However, despite this, fluorinated pyridine and pyrimidine nuclei remain relatively understudied and their effects on drug properties relatively undocumented.

There is therefore a need to provide new antimicrobial compounds, which incorporate fluorine.

The present invention arose due to the inventor's interest in the development of methodologies to incorporate fluorinated pyridine and pyrimidine nuclei into drug structures with a strong provenance to act as the basis for the development of novel screening collections. The inventors believe the chemical family they have identified is novel per se.

Hence, in a first aspect of the invention, there is provided a compound of formula (I):

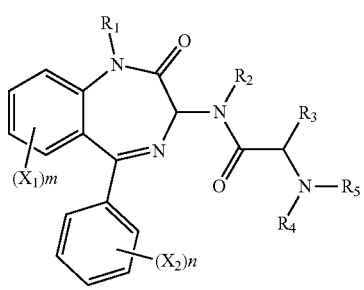

Formula (I)

wherein $R_1$ is H or a $C_{1-5}$ straight or branched alkyl or alkenyl;
$R_2$ is H or a $C_{1-5}$ straight or branched alkyl or alkenyl;
$R_3$ is any amino acid side chain; and $R_4$ is H or a $C_{1-5}$ straight or branched alkyl or alkenyl; or $R_3$ and $R_4$, together with the atoms to which they are attached, combine to form a five-membered heterocyclic ring;

$R_5$ is a six membered ring optionally substituted with one or more substituents, wherein the or each substituent is independently a $C_{1-5}$ straight or branched alkyl or alkenyl, a halogen, $SR_6$, $SO_2R_6$, $OR_6$, or $NR_6R_7$;
m is 0, 1, 2, 3 or 4;
n is 0, 1, 2, 3, 4 or 5;
the or each $X_1$ is independently selected from a $C_{1-5}$ straight or branched alkyl or alkenyl, a halogen, $SR_6$, $SO_2R_6$, $OR_6$ or $NR_6R_7$;
the or each $X_2$ is independently selected from a $C_{1-5}$ straight or branched alkyl or alkenyl, a halogen, $SR_6$, $SO_2R_6$, $OR_6$ or $NR_6R_7$;
the or each $R_6$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

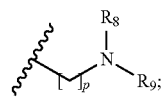

the or each $R_7$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

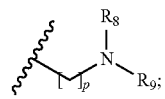

and/or $R_6$ and $R_7$ together with the nitrogen atom to which they are attached independently form a 3-7 membered ring which is optionally substituted with one or more substituents, wherein the or each substituent is independently a $C_{1-5}$ straight or branched alkyl or alkenyl, a halogen, $C(O)R_{10}$, $SR_{10}$, $SO_2R_{10}$, $OR_{10}$ or $NR_{10}R_{11}$; the or each $R_{10}$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

the or each $R_{11}$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

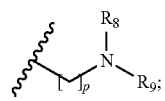

p is 1, 2, 3, 4 or 5; and
$R_8$ and $R_9$ together with the nitrogen atom to which they are attached independently form a 3-7 membered ring;
or a pharmaceutically acceptable salt, solvate, tautomeric form or polymorphic form thereof.

The inventors have found that compounds of formula (I) may be useful in therapy or as a medicament.

Hence, in a second aspect, there is provided a compound of formula (I) or a pharmaceutically acceptable salt, solvate, tautomeric form or polymorphic form thereof, for use in therapy.

The inventors have also found that compounds of formula (I) are useful in the treatment of microbial infections.

Hence, in a third aspect, there is provided a compound of formula (I) or a pharmaceutically acceptable salt, solvate, tautomeric form or polymorphic form thereof, for use in treating, ameliorating, or preventing a microbial infection.

In a fourth aspect, there is provided a method of treating, ameliorating or preventing a microbial infection, the method comprising administering, to a subject in need of such treatment, a therapeutically effective amount of a compound of formula (I) or a pharmaceutically acceptable salt, solvate, tautomeric form or polymorphic form thereof.

The term "pharmaceutically acceptable salt" may be understood to refer to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminium ion, or alkali metal or alkaline earth metal hydroxides, such as sodium, potassium, calcium, magnesium, aluminium, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts may include, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "solvate" may be understood to refer to a compound provided herein or a salt thereof, that further includes a stoichiometric or non-stoichiometric amount of solvent bound by non-covalent intermolecular forces. Where the solvent is water, the solvate is a hydrate.

In one embodiment, the microbial infection which may be treated by the compound of Formula (I) may comprise a fungal infection.

Alternatively, in a preferred embodiment, the microbial infection which may be treated by the compound of Formula (I) may comprise a bacterial infection. The bacterial infection may comprise a gram-positive bacterial infection. Alternatively, the bacterial infection may comprise a gram-negative bacterial infection.

Preferably, however, the microbial infection which may be treated preferably comprises a viral infection. Examples of a viral infection which may be treated with compounds of the invention include: Respiratory Syncytial Virus (RSV), Hepatitis C Virus (HCV), Dengue Virus, Ebola virus, Hepatitis B Virus, and Influenza virus. In a preferred embodiment, the compound is for use in treating, ameliorating, or preventing an infection caused by Respiratory Syncytial Virus (RSV).

It will be understood that $R_1$ may be a methyl group, an ethyl group, a propyl group, a butyl group or a pentyl group. In one preferred embodiment, $R_1$ is a methyl group.

However, in a more preferred embodiment, $R_1$ is a hydrogen, and the compound has the formula (Ia):

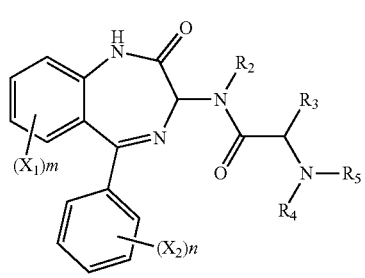

Formula (Ia)

It will be understood that $R_2$ may be a methyl group, an ethyl group, a propyl group, a butyl group or a pentyl group. Similarly, it will be understood that $R_4$ may be a methyl group, an ethyl group, a propyl group, a butyl group or a pentyl group.

In one preferred embodiment, $R_2$ is a methyl group. In one preferred embodiment, $R_4$ is methyl group.

However, in a more preferred embodiment, $R_2$ is a hydrogen. In a more preferred embodiment, $R_4$ is hydrogen.

In a further preferred embodiment, both $R_2$ and $R_4$ are hydrogen and the compound has the formula (Ib):

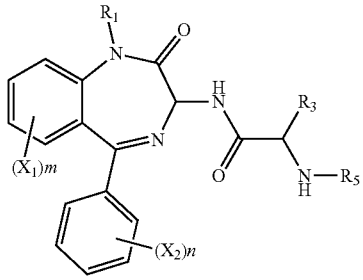

Formula (Ib)

In a preferred embodiment, m is 0 and the compound has a formula (Ic):

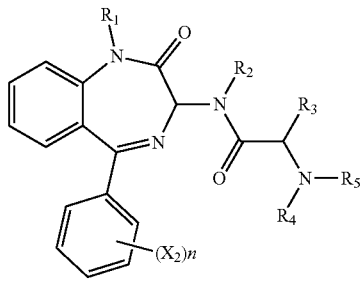

Formula (Ic)

In an alternative embodiment, m is 4. Accordingly, an $X_1$ group will be present on each of the position 6, 7, 8 and 9 carbons of the benzodiazepine ring structure.

In an embodiment where m is 1, then an $X_1$ group may be bonded to one of the position 6, 7, 8 and 9 carbons of the benzodiazepine ring structure, and a hydrogen will be bonded to each of the three remaining carbons. In an embodiment where m is 2, then an $X_1$ group may be bonded to two of the position 6, 7, 8 and 9 carbons of the benzodiazepine ring structure, and a hydrogen will be bonded to each of the two remaining carbons. In an embodiment where m is 3, then an $X_1$, group may be bonded to three of the position 6, 7, 8 and 9 carbons of the benzodiazepine ring structure, and a hydrogen will be bonded to the remaining carbon.

In an alternative preferred embodiment, m is 1, and the $X_1$ group is bonded to the 7 position carbon and the compound has a formula (Id):

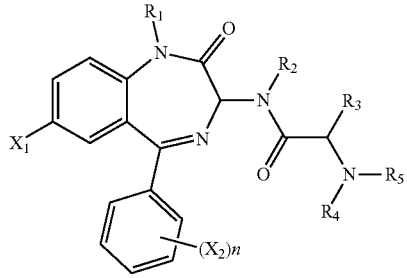

Formula (Id)

$X_1$ may be any halogen, such as fluorine, chlorine, bromine or iodine. Preferably, X is chlorine or fluorine. In a preferred embodiment, m is 1, and the $X_1$ is a chlorine bonded to the 7 position carbon.

In a preferred embodiment, n is 0 and the compound has a formula (Ie):

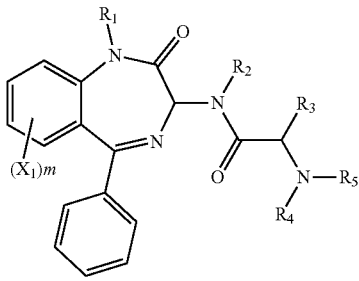

Formula (Ie)

In an embodiment where n is 5, then an $X_2$ group will be present on each of the position 2, 3, 4, 5 and 6 carbons of the phenyl ring structure.

In an embodiment where n is 1, then an $X_2$ group may be bonded to one of the position 2, 3, 4, 5 and 6 carbons of the phenyl ring structure, and a hydrogen will be bonded to each of the four remaining carbons. In an embodiment where n is 2, then an $X_2$ group may be bonded to two of the position 2, 3, 4, 5 and 6 carbons of the phenyl ring structure, and a hydrogen will be bonded to each of the three remaining carbons. In an embodiment where n is 3, then an $X_2$ group may be bonded to three of the position 2, 3, 4, 5 and 6 carbons of the phenyl ring structure, and a hydrogen will be bonded to the two remaining carbons. In an embodiment where n is 4, then an $X_2$ group may be bonded to four of the position 2, 3, 4, 5 and 6 carbons of the phenyl ring structure, and a hydrogen will be bonded to the remaining carbon.

In an alternative preferred embodiment, n is 1, and the $X_2$ group is bonded to the 4 position carbon.

$X_2$ may be any halogen, such as fluorine, chlorine, bromine or iodine. Preferably, $X_2$ is chlorine. Alternatively, $X_2$ is preferably fluorine. Alternatively, $X_2$ is preferably bromine.

It will be appreciated that $R_3$ is the side chain of any amino acid. Preferably, $R_3$ is the side chain of any naturally occurring amino acid. $R_3$ may be an arginine side chain, a histidine side chain, a lysine side chain, an aspartic acid side chain, a glutamic acid side chain, a serine side chain, a threonine side chain, an asparagine side chain, a glutamine side chain, a cysteine side chain, a cysteine side chain, a selenocysteine side chain, a glycine side chain, a proline side chain, an alanine side chain, a valine side chain, an isoleucine side chain, a leucine side chain, a methionine side chain, a phenylalanine side chain, a tyrosine side chain or a tryptophan side chain.

By way of example, it will be appreciated that a glycine side chain is hydrogen, an alanine is methyl, a valine is isopropyl, and a phenylalanine is benzyl. Alternatively, when $R_3$ is proline side chain then $R_3$ and $R_4$, together with the atoms to which they are attached, combine to form a five-membered heterocyclic ring.

In one embodiment, $R_3$ may be a nucleophilic amino acid side chain, which may be selected from serine, threonine and cysteine. Preferably, however, $R_3$ is not a cysteine side chain. In another embodiment, $R_3$ may be a hydrophobic amino acid side chain, which may be selected from valine, leucine, isoleucine, methionine and proline. In yet another embodiment, $R_3$ may be an aromatic amino acid side chain, which may be selected from phenylalanine, tyrosine, tryptophan, aspartic acid and glutamic acid. In yet another embodiment, $R_3$ may be an amide amino acid side chain, which may be selected from asparagine and glutamine. In yet another embodiment, $R_3$ may be a basic amino acid side chain, which be selected from histidine, lysine and arginine. In yet another embodiment, $R_3$ may be the side chain of a small amino acid, which may be either glycine or alanine.

In a preferred embodiment, $R_3$ is a glycine side chain, i.e. $R_3$ is a hydrogen, and the compound has the formula (Ifa):

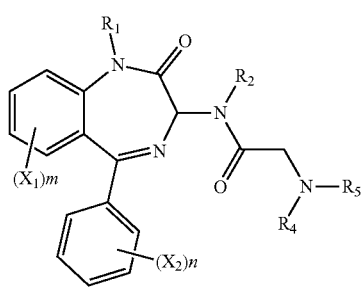

Formula (Ifa)

In an alternative preferred embodiment, $R_3$ is an alanine side chain, i.e. $R_3$ is a methyl, and the compound has the formula (Ifb):

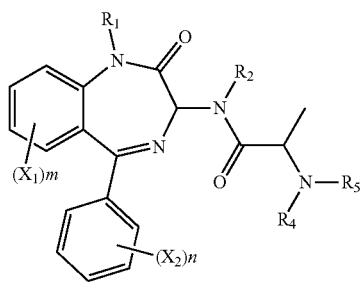

Formula (Ifb)

In a further alternative preferred embodiment, $R_3$ is a valine side chain, i.e. $R_3$ is an isopropyl, and the compound has the formula (Ifc):

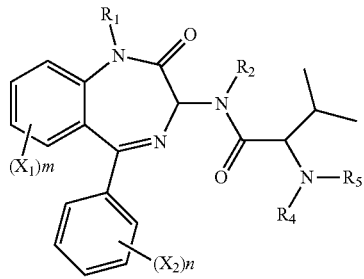

Formula (Ifc)

In a still further alternative preferred embodiment, $R_3$ is a phenylalanine side chain, i.e. $R_3$ is a phenyl, and the compound has the formula (Ifd):

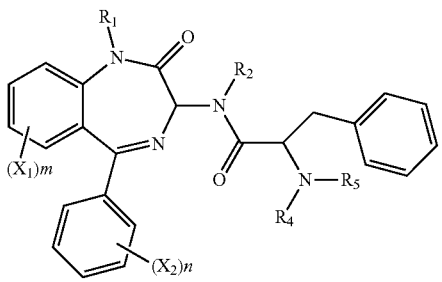

Formula (Ifd)

In a still further alternative preferred embodiment, $R_3$ is proline side chain, i.e. $R_3$ and $R_4$, together with the atoms to which they are attached, combine to form a five-membered heterocyclic ring, and the compound has the formula (Ife):

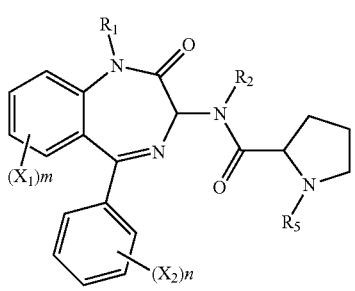

Formula (Ife)

It will be appreciated that the compound of Formula (I) comprises an amino acid linker, i.e.:

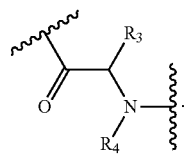

The amino acid linker may be a D amino acid linker, i.e.:

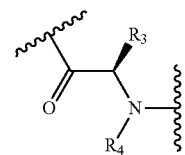

However, in a preferred embodiment the amino acid linker is an L amino acid linker, i.e.:

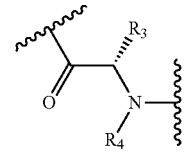

Preferably, $R_5$ is an aromatic ring optionally substituted with one or more substituents.

Accordingly, $R_5$ may be a phenyl, a pyridinyl, pyrazinyl, pyridazinyl or a pyrimidinyl group optionally substituted with one or more substituents. More preferably, $R_5$ is a phenyl, pyridine or pyrimidine optionally substituted with one or more substituents. Accordingly, $R_5$ may be selected from the group consisting of:

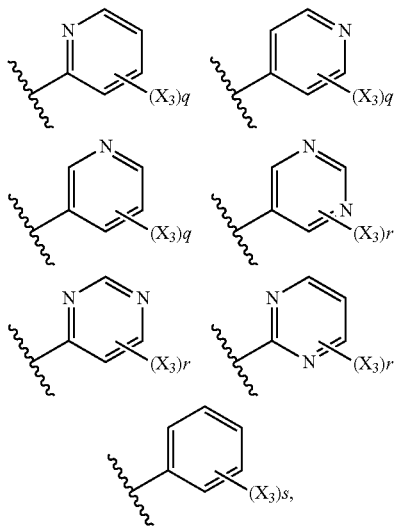

wherein:
q is 0, 1, 2, 3 or 4;
r is 0, 1, 2 or 3;
s is 0, 1, 2, 3, 4 or 5; and
$X_3$ is independently a $C_{1-5}$ straight or branched alkyl or alkenyl, a halogen, $SR_6$, $SO_2R_6$, $OR_6$, or $NR_6R_7$.

Preferably, $R_5$ is selected from the group consisting of:

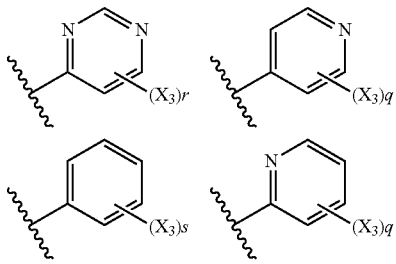

Preferably, the phenyl, pyridinyl or pyrimidinyl group is substituted with one or more $X_3$ groups.

It will be appreciated that when $X_3$ is a $C_{1-5}$ straight or branched alkyl or alkenyl then $X_3$ may be a methyl group, an ethyl group, a propyl group, a butyl group or a pentyl group.

It will be appreciated that when $X_3$ is a halogen then $X_3$ may be fluorine, chlorine, bromine or iodine.

It will be appreciated that when $R_6$ and/or $R_7$ is a $C_{1-5}$ straight or branched alkyl or alkenyl then $R_6$ and/or $R_7$ may independently be a methyl group, an ethyl group, a propyl group, a butyl group or a pentyl group.

When $R_6$ and/or $R_7$ is a $C_{3-6}$ cycloalkyl or cycloalkenyl, the or each $C_{3-6}$ cycloalkyl or cycloalkenyl may independently be cyclohexyl or phenyl.

When $R_6$ and/or $R_7$ is a $C_{3-6}$ heterocyclyl or heteroaryl, the or each $C_{3-6}$ heterocyclyl or heteroaryl may independently be pyridyl, pyrimidyl, furanyl, imidazolyl, piperidinyl, morpholinyl, pyrrolidinyl, thiomorpholinyl or thiomorpholinyl S,S dioxide.

Preferably, when $X_3$ is $SR_6$ then $R_6$ is a $C_{1-5}$ straight or branched alkyl or alkenyl, and more preferably $R_6$ is a methyl group.

Preferably, when $X_3$ is $SO_2R_6$ then $R_6$ is a $C_{1-5}$ straight or branched alkyl or alkenyl, and more preferably $R_6$ is a methyl group.

Preferably, when $X_3$ is $OR_6$ then $R_6$ is a $C_{1-5}$ straight or branched alkyl or alkenyl, and more preferably $R_6$ is an ethyl group.

In one embodiment, when $X_3$ is $NR_6R_7$ then $R_6$ is a $C_{1-5}$ straight or branched alkyl or alkenyl and $R_7$ is hydrogen. Preferably, $R_6$ is a methyl group, an ethyl group or a propyl group.

In an alternative embodiment, when $X_3$ is $NR_6R_7$ then $R_6$ is a $C_{1-5}$ straight or branched alkyl or alkenyl and $R_7$ is a $C_{1-5}$ straight or branched alkyl or alkenyl. Preferably, $R_6$ and $R_7$ are each independently a methyl group, an ethyl group or a propyl group. In one embodiment, both $R_6$ and $R_7$ are an ethyl group.

In an alternative embodiment, when $X_3$ is $NR_6R_7$ then $R_6$ and $R_7$ together with the nitrogen atom to which they are attached independently form a 3-7 membered ring which is optionally substituted with one or more substituents. The or each 3-7 membered ring may be a 4 membered ring, a 5 membered ring or a 6 membered ring which is optionally substituted with one or more substituents. The four membered ring may be azetidine which is optionally substituted with one or more substituents. The 5 membered ring may be pyrrolidine which is optionally substituted with one or more substituents. The 6 membered ring may be piperidine, piperazine, morpholine, thiomorpholine or thiomorpholine S,S dioxide which is optionally substituted with one or more substituents.

The 3-7 membered ring may be substituted with a $C_{1-5}$ straight or branched alkyl or alkenyl. The $C_{1-5}$ straight or branched alkyl or alkenyl may independently be a methyl group, an ethyl group, a propyl group, a butyl group or a pentyl group.

The 3-7 membered ring may be substituted with a halogen. The halogen may be fluorine, chlorine, bromine or iodine. Preferably, the halogen is fluorine or chlorine. In some embodiments, the 3-7 membered ring may be:

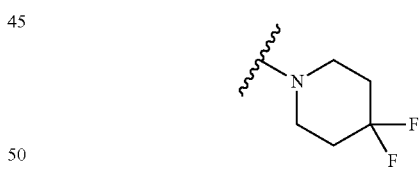

The 3-7 membered ring may be substituted with $C(O)R_{10}$. $R_{10}$ may be a methyl group, an ethyl group, a propyl group, a butyl group or a pentyl group. Preferably, $R_{10}$ is a methyl group. In some embodiments, the 3-7 membered ring may be:

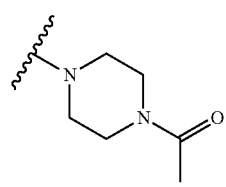 [SMILES: *N1CCN(C(C)=O)CC1]

The 3-7 membered ring may be substituted with $SR_{10}$ or $SO_2R_{10}$. $R_{10}$ may be a methyl group, an ethyl group, a propyl group, a butyl group or a pentyl group. Preferably, $R_{10}$ is a methyl group. In some embodiments, the 3-7 membered ring may be:

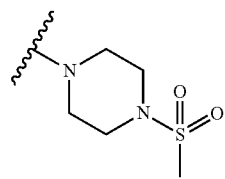 [SMILES: *N1CCN(S(C)(=O)=O)CC1]

The 3-7 membered ring may be substituted with $OR_{10}$. $R_{10}$ may be a methyl group, an ethyl group, a propyl group, a butyl group or a pentyl group.

The 3-7 membered ring may be substituted with $NR_{10}R_{11}$. $R_{10}$ and $R_{11}$ may each independently be a methyl group, an ethyl group, a propyl group, a butyl group or a pentyl group.

When $R_6$ and/or $R_7$ is

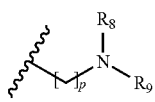

then $R_8$ and $R_9$ together with the nitrogen atom to which they are attached independently form a 3-7 membered ring. The or each 3-7 membered ring may be a 4 membered ring, a 5 membered ring or a 6 membered ring. The four membered ring may be azetidine. The 5 membered ring may be pyrrolidine. The 6 membered ring may be piperidine, piperazine, morpholine, thiomorpholine or thiomorpholine S,S dioxide. Preferably, $R_8$ and $R_9$ together with the nitrogen atom to which they are attached independently form morpholine.

In one preferred embodiment $R_5$ is a phenyl group, optionally substituted with one or more $X_3$ groups, and the compound has formula (Ig):

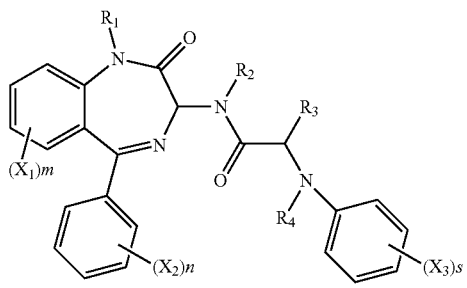

Formula (Ig)

In one embodiment s is 5. Preferably, at least one $X_3$ group is a halogen. More preferably, at least two $X_3$ groups are halogens, at least three $X_3$ groups are halogens, or at least four $X_3$ groups are halogens. Most preferably, all $X_3$ groups are halogens. Preferably, the or each halogen is a fluorine.

However, in a more preferred embodiment $R_5$ is a phenyl group, s is 0 and the compound has formula (Ih):

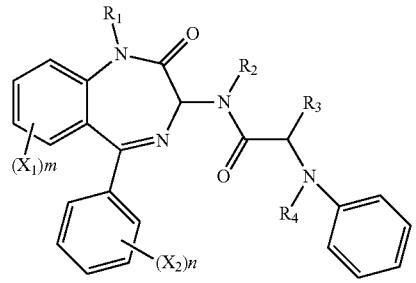

Formula (Ih)

In one preferred embodiment $R_5$ is a pyridinyl group, optionally substituted with one or more $X_3$ groups. The compound may have formula (Ii):

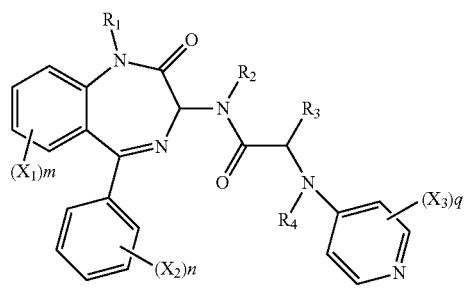

Formula (Ii)

Alternatively, the compound may have formula (Iia):

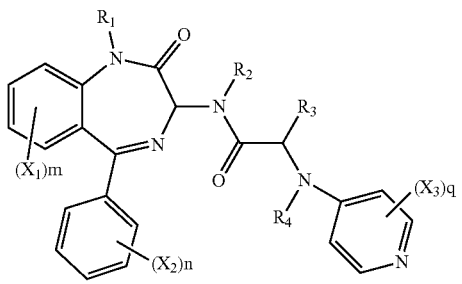

Formula (Iia)

In a more preferred embodiment $R_5$ is a pyridinyl group and q is 4. The compound may have formula (Ij) or (Ija):

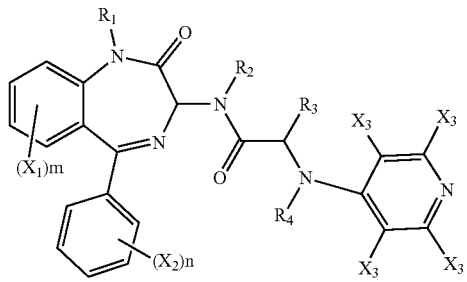

Formula (Ij)

Formula (Ija)

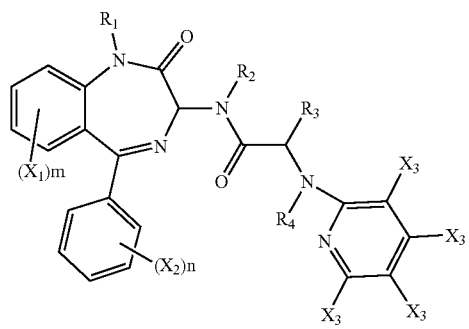

Preferably, at least one $X_3$ group is a halogen. More preferably, at least two $X_3$ groups are halogens. Even more preferably, at least three $X_3$ groups are halogens. Preferably, the or each halogen is a fluorine.

In one preferred embodiment, $R_5$ is a pyridinyl group, q is 4, three $X_3$ groups are a halogen and one $X_3$ group comprises $OR_6$. Preferably, each halogen is fluorine. Preferably, $R_6$ is an ethyl group. Preferably, the compound has formula (Ik):

Formula (Ik)

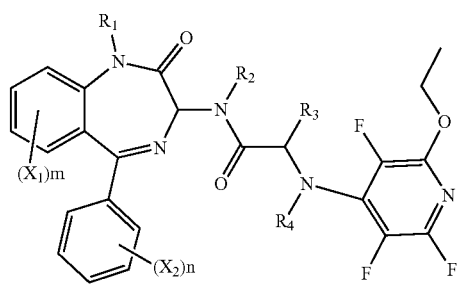

In a more preferred embodiment, $R_5$ is a pyridinyl group, q is 4 and each of the four $X_3$ groups is a halogen. Preferably, each halogen is fluorine. The compound may have formula (Il):

Formula (Il)

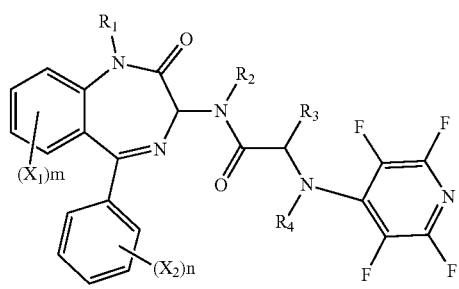

In a further preferred embodiment, $R_5$ is a pyridinyl group, q is 4, three $X_3$ groups are a halogen and one $X_3$ group comprises $SO_2R_6$. Preferably, each halogen is fluorine. Preferably, $R_6$ is an methyl group. Preferably, each halogen is fluorine. Preferably, the compound has formula (IIa):

Formula (IIa)

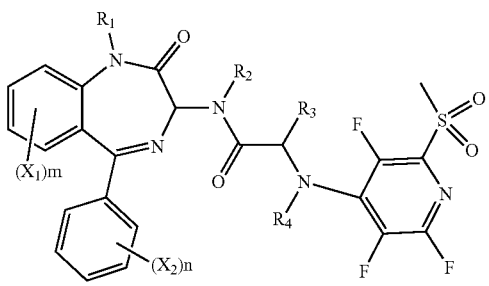

In a further preferred embodiment, $R_5$ is a pyridinyl group, q is 4, three $X_3$ groups are a halogen and one $X_3$ group comprises $NR_6R_7$. Preferably, each halogen is fluorine. $R_6$ and $R_7$ may each independently be a hydrogen or a $C_{1-5}$ straight or branched alkyl or alkenyl. Preferably, $R_6$ and $R_7$ may each independently be methyl, ethyl, propyl, butyl or pentyl. More preferably $R_6$ and $R_7$ are each ethyl. Preferably, the compound has formula (IIb):

Formula (IIb)

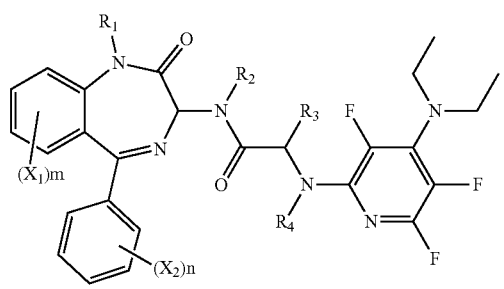

Alternatively, $R_6$ and $R_7$ together with the nitrogen atom to which they are attached independently form a 3-7 membered ring which is optionally substituted with one or more substituents. Preferably, $R_6$ and $R_7$ together with the nitrogen atom to which they are attached independently form a piperazine ring which is optionally substituted with one or more substituents. Preferably, the piperazine ring is substituted with $C(O)R_{10}$, and more preferably $R_{10}$ is methyl. Preferably, the compound has formula (IIc):

Formula (IIc)

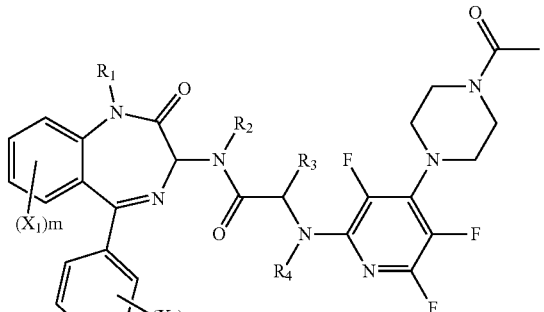

Alternatively, $R_6$ and $R_7$ together with the nitrogen atom to which they are attached independently form a thiomorpholinyl S,S dioxide ring which is optionally substituted with one or more substituents. Preferably, the thiomorpholinyl S,S dioxide ring is unsubstituted. Preferably, the compound has formula (IId):

Formula (IId)

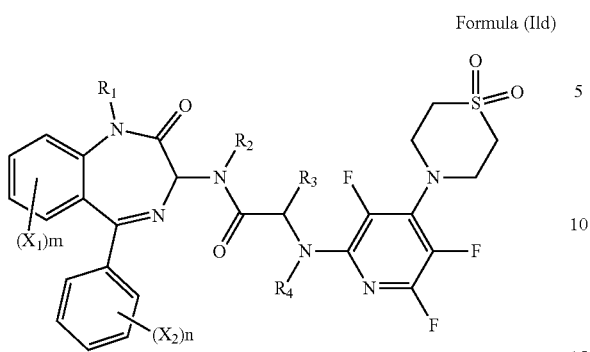

Alternatively, $R_6$ and $R_7$ together with the nitrogen atom to which they are attached independently form a morpholine ring which is optionally substituted with one or more substituents. Preferably, the morpholine ring is unsubstituted. Preferably, the compound has formula (IIe):

Formula (IIe)

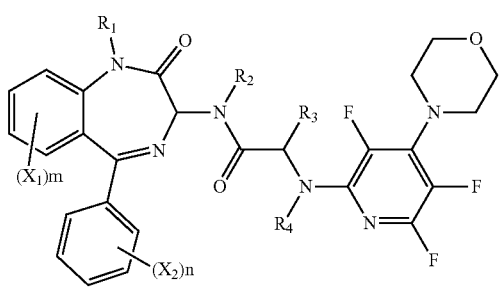

Alternatively, $R_6$ and $R_7$ together with the nitrogen atom to which they are attached independently form a piperidine ring which is optionally substituted with one or more substituents. Preferably, the piperidine ring is substituted with at least one halogen. Preferably, the peperidine ring is substituted with 1, 2, 3, 4, 5, 6, 7, 8, 9 or 10 halogens. Preferably, the or each halogen in fluorine. Preferably, the compound has formula (IIf):

Formula (IIf)

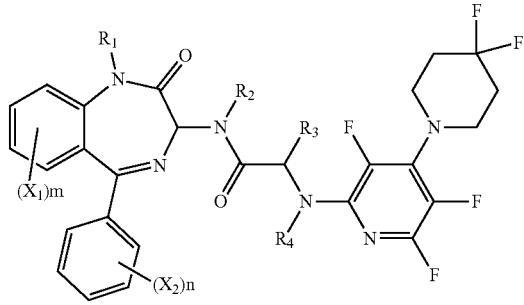

In an alternative preferred embodiment, $R_5$ is a pyrimidine group, optionally substituted with one or more $X_3$ groups. The compound may have formula (IIg):

Formula (IIg)

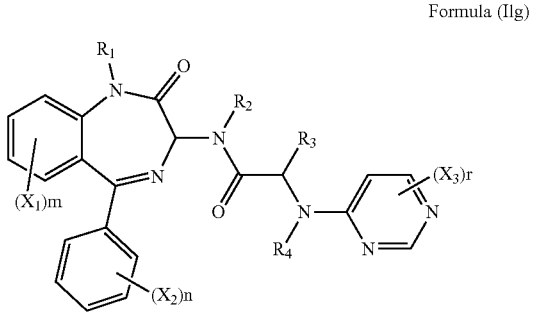

It will be appreciated that r may be 1, 2 or 3. In a preferred embodiment, $R_5$ is a pyrimidine group and r is 1. The compound may have formula (IIh):

Formula (IIh)

Preferably, $X_3$ is a halogen or $SO_2R_6$. More preferably, $X_3$ is a chlorine or $SO_2Me$. It will be appreciated that compounds described herein possess a chiral centre at the position 3 carbon of the benzodiazepine ring structure. Accordingly, in one preferred embodiment, the compound may have an S chiral centre and a formula (Im):

Formula (Im)

In a preferred embodiment, $R_1$ is hydrogen, $R_2$ is hydrogen, $R_3$ is hydrogen, $R_4$ is hydrogen, L is absent, $R_5$ is a phenyl group, m is 0, n is 0, s is 0 and the compound has an S chiral centre. Accordingly, the compound may have formula (In):

Formula (In)

In an alternative preferred embodiment, $R_1$ is hydrogen, $R_2$ is hydrogen, $R_3$ is hydrogen, $R_4$ is hydrogen, L is absent, $R_5$ is a pyridinyl group, m is 0, n is 0, q is 4, three $X_3$ groups are fluorine, one $X_3$ group is $OR_8$, $R_8$ is ethyl and the compound has an S chiral centre. Accordingly, the compound may have formula (Io):

Formula (Io)

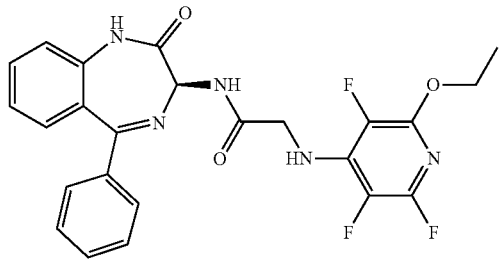

In a further alternative preferred embodiment, $R_1$ is hydrogen, $R_2$ is hydrogen, $R_3$ is hydrogen, $R_4$ is hydrogen, L is absent, $R_5$ is a pyridinyl group, m is 0, n is 0, q is 4 and all $X_3$ groups are fluorine. Accordingly, the compound may have formula (Ip):

Formula (Ip)

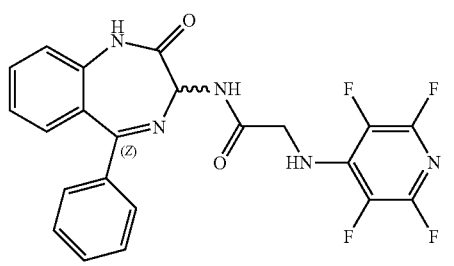

In a most preferred embodiment, $R_1$ is hydrogen, $R_2$ is hydrogen, $R_3$ is hydrogen, $R_4$ is hydrogen, L is absent, $R_5$ is a pyridinyl group, m is 0, n is 0, q is 4, all $X_3$ groups are fluorine and the compound has an S chiral centre. Accordingly, the compound may have formula (Iq):

Formula (Iq)

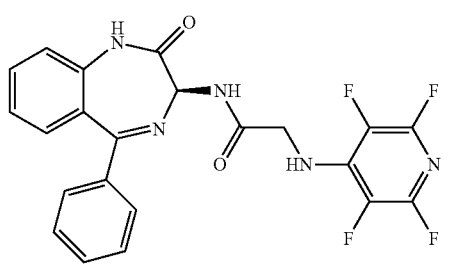

Alternatively, the compound may be selected from:

Formula (Ira)

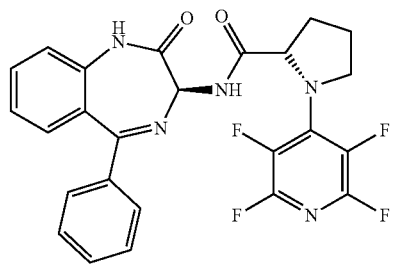

Formula (Irb)

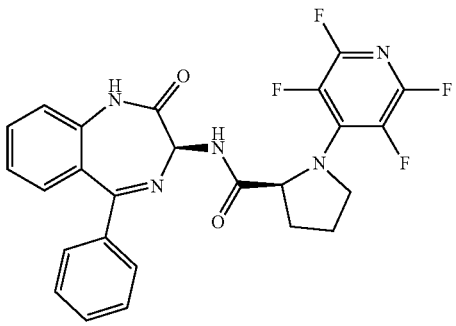

Formula (Irc)

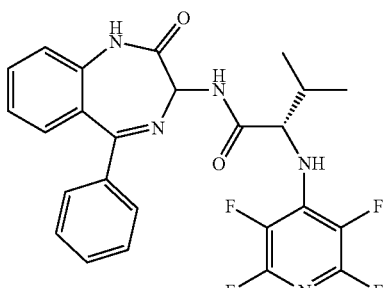

Formula (Ird)

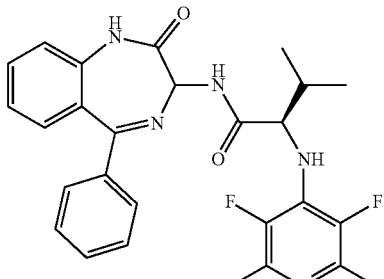

Formula (Ire)

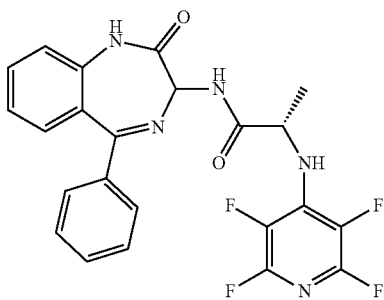

Formula (Irf)

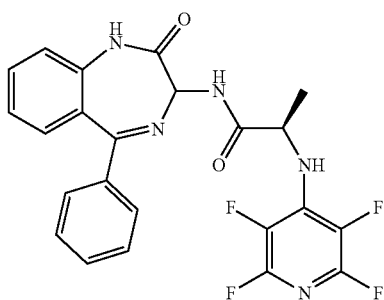

-continued
Formula (Irg)
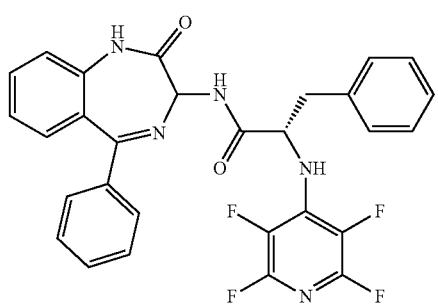
Formula (Irh)
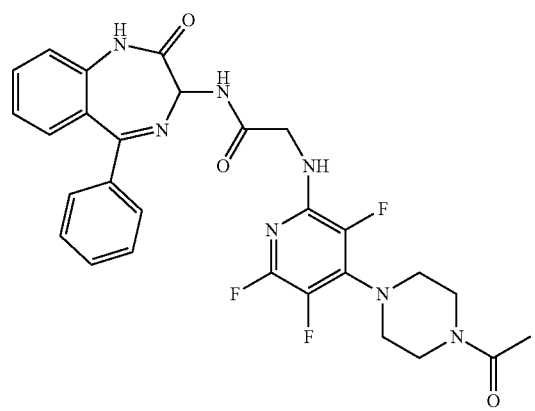
Formula (Iri)
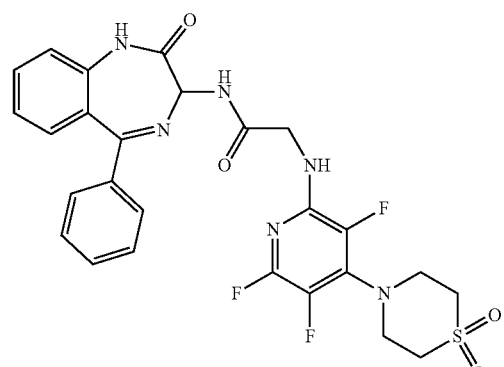
Formula (Irj)
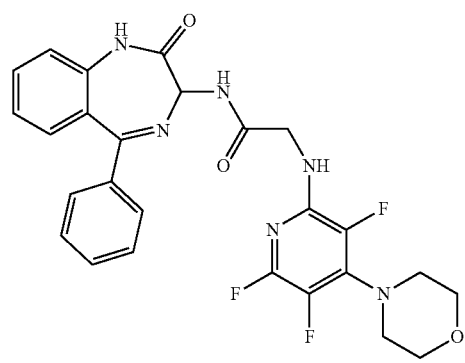
-continued
Formula (Irk)
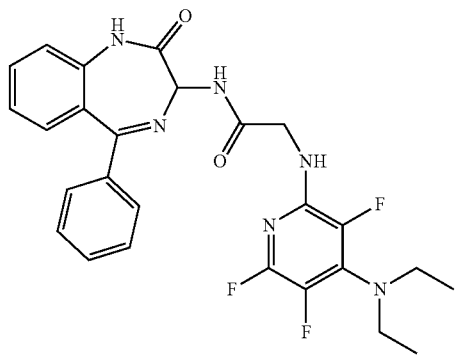
Formula (Irl)
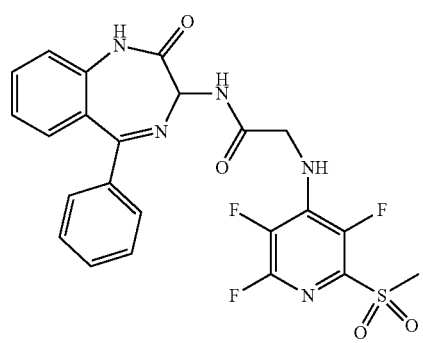
Formula (Irm)
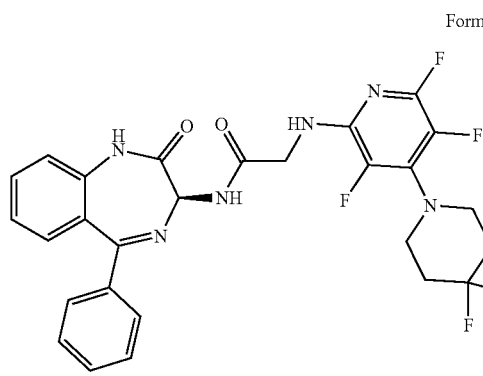
Formula (Irn)
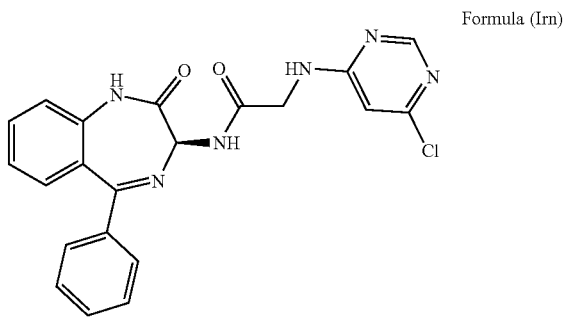

-continued

Formula (Iro)

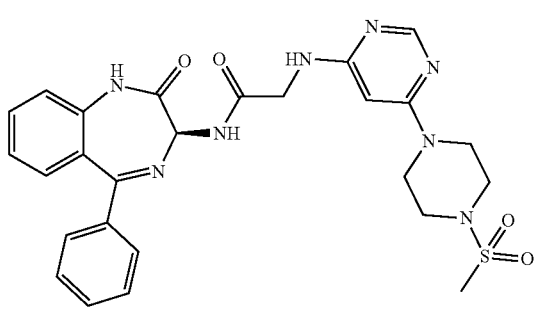

It will be appreciated that the compounds described herein or a pharmaceutically acceptable salt, solvate, tautomeric form or polymorphic form thereof may be used in a medicament which may be used in a monotherapy (i.e. use of the compound alone), for treating, ameliorating, or preventing a microbial infection. Alternatively, the compounds or a pharmaceutically acceptable salt, solvate, tautomeric form or polymorphic form thereof may be used as an adjunct to, or in combination with, known therapies for treating, ameliorating, or preventing a microbial infection. For example, known antivirals for treating respiratory syncytial virus (RSV), which may be administered with compounds of Formula I, include ribavirin or bronchodilators.

The compounds may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

Medicaments comprising the compounds described herein may be used in a number of ways. For instance, oral administration may be required, in which case the compound may be contained within a composition that may, for example, be ingested orally in the form of a tablet, capsule or liquid. Compositions comprising the compounds of the invention may be administered by inhalation (e.g. intranasally). Compositions may also be formulated for topical use. For instance, creams or ointments may be applied to the skin.

Compounds according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with compounds used according to the invention is required and which would normally require frequent administration (e.g. at least daily injection).

In a preferred embodiment, compounds and compositions according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the compound that is required is determined by its biological activity and bioavailability, which in turn depends on the mode of administration, the physiochemical properties of the compound, and whether it is being used as a monotherapy, or in a combined therapy. The frequency of administration will also be influenced by the half-life of the compound within the subject being treated. Optimal dosages to be administered may be determined by those skilled in the art, and will vary with the particular compound in use, the strength of the pharmaceutical composition, the mode of administration, and the advancement of the a microbial infection. Additional factors depending on the particular subject being treated will result in a need to adjust dosages, including subject age, weight, gender, diet, and time of administration.

Generally, a daily dose of between 0.01 g/kg of body weight and 500 mg/kg of body weight of the compound according to the invention may be used for treating, ameliorating, or preventing a microbial infection depending upon which compound or analogue is used. More preferably, the daily dose is between 0.01 mg/kg of body weight and 400 mg/kg of body weight, more preferably between 0.1 mg/kg and 200 mg/kg body weight, and most preferably between approximately 1 mg/kg and 100 mg/kg body weight.

The compound may be administered before, during or after onset of the microbial infection to be treated. Daily doses may be given as a single administration (e.g. a single daily injection). Alternatively, the microbial infection may require administration twice or more times during a day. As an example, compounds according to the invention may be administered as two (or more depending upon the severity of the microbial infection being treated) daily doses of between 25 mg and 7000 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of the compounds according to the invention to a patient without the need to administer repeated doses.

Known procedures, such as those conventionally employed by the pharmaceutical industry (e.g. in vivo experimentation, clinical trials, etc.), may be used to form specific formulations comprising the compounds according to the invention and precise therapeutic regimes (such as daily doses of the compounds and the frequency of administration). The inventors believe that they are the first to describe a pharmaceutical composition for treating a microbial infection, based on the use of the compounds of the invention.

Hence, in a fifth aspect of the invention, there is provided a pharmaceutical composition comprising a compound according to the first aspect, or a pharmaceutically acceptable salt, solvate, tautomeric form or polymorphic form thereof, and a pharmaceutically acceptable vehicle.

The pharmaceutical composition can be used in the therapeutic amelioration, prevention or treatment in a subject of a microbial infection. Thus, the composition is preferably an antimicrobial pharmaceutical composition, most preferably an antiviral pharmaceutical composition. In a most preferred embodiment, the composition of the fifth aspect is an anti-RSV pharmaceutical composition. Preferably, the compound has any of the formulae shown as formula I, Ia-Iq.

The invention also provides, in a sixth aspect, a process for making the composition according to the fifth aspect, the process comprising contacting a therapeutically effective amount of a compound of the first aspect, or a pharmaceutically acceptable salt, solvate, tautomeric form or polymorphic form thereof, and a pharmaceutically acceptable vehicle.

Preferably, the compound has any of the formulae shown as formula I, Ia-Iq.

A "subject" may be a vertebrate, mammal, or domestic animal. Hence, compounds, compositions and medicaments according to the invention may be used to treat any mammal, for example livestock (e.g. a horse), pets, or may be used in other veterinary applications. Most preferably, however, the subject is a human being.

A "therapeutically effective amount" of compound is any amount which, when administered to a subject, is the amount of drug that is needed to treat the target disease, or produce the desired effect, i.e. inhibit microbial infections, preferably RSV infections.

For example, the therapeutically effective amount of compound used may be from about 0.01 mg to about 800 mg, and preferably from about 0.01 mg to about 500 mg. It is preferred that the amount of compound is an amount from about 0.1 mg to about 250 mg, and most preferably from about 0.1 mg to about 20 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents (i.e. the compound according to the first, second and third aspects) according to the invention. In tablets, the active compound may be mixed with a vehicle having the necessary compression properties in suitable proportions and compacted in the shape and size desired. The powders and tablets preferably contain up to 99% of the active compound. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The compound according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The compound may be prepared as a sterile solid composition that may be dissolved or suspended at the time of administration using sterile water, saline, or other appropriate sterile injectable medium.

The compound and compositions of the invention may be administered in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compounds used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The inventors believe that their method of manufacturing the compound of the first aspect is also novel.

In accordance with a seventh aspect there is provided a method of manufacturing the compound of the first aspect, the method comprising contacting a compound of formula (II), or a salt or solvate thereof:

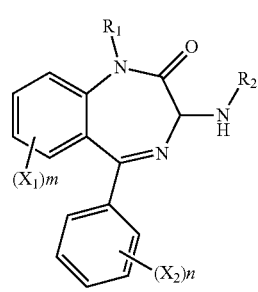

Formula (II)

with a compound of formula (III), or a salt or solvate thereof:

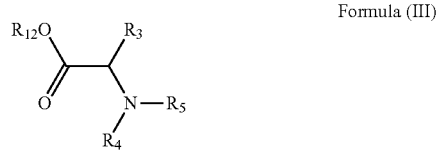

Formula (III)

wherein $R_1$, $R_2$, $R_3$, $R_4$, $R_5$, $X_1$, $X_2$, m and n are as defined above; and $R_{12}$ is H or a $C_{1-5}$ straight or branched alkyl or alkenyl.

It will be understood that $R_{12}$ may be a methyl group, an ethyl group, a propyl group, a butyl group or a pentyl group. In one preferred embodiment, $R_{12}$ is a methyl group.

However, in a more preferred embodiment, $R_{12}$ is a hydrogen.

Preferably, the compound of Formula (III) is a compound of Formula (IIIa):

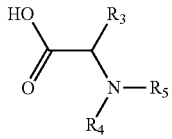

Formula (IIIa)

More preferably, the compound of Formula (III) is a compound of Formula (IIIb):

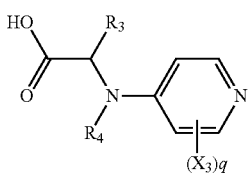

Formula (IIIb)

Most preferably, the compound of Formula (III) is a compound of Formula (IIIc):

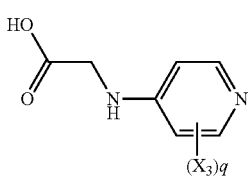

Formula (IIIc)

Preferably, the compounds of Formula (II) and Formula (III) are contacted in the presence of a base. Preferably, the base is trimethylamine.

Preferably, the compounds of Formula (II) and Formula (III) are contacted in the presence of a coupling reagent. Preferably, the coupling reagent is 2-(1H-benzotriazol-1-yl)-1,1,3,3-tetramethyluronium hexafluorophosphate (HBTU).

The reaction may be carried out in a solution comprising dimethyl formamide (DMF), tetrahydrofuran (THF) and/or acetonitrile. Preferably, the reaction is carried out in a solution comprising dimethyl formamide.

Preferably, the solution is stirred for at least 1 hour. More preferably, the solution is stirred for at least 2, 3, 4 or 5 hours. Most preferably, the solution is stirred for at least or 15 hours.

Preferably, the solution is stirred at a temperature between 0° C. and 50° C. More preferably, the solution is stirred at a temperature between 5° C. and 40° C. or between 10° C. and 30° C. Most preferably, the solution is stirred at about room temperature.

The method may comprise subsequently contacting the resultant compound with a nucleophile. The nucleophile may comprise an alcohol, a thiol, a thiolate, an amine or a salt thereof. The alcohol may comprise methanol, ethanol, propanol, butanol or pentanol. The thiol may comprise methanethiol, ethanethiol, propanethiol, butanthiol or pentanthiol. The thiolate may comprise methanethiolate, ethanethiolate, propanethiolate, butanthiolate or pentanthiolate. The amine may comprise pyrrolidine, piperidine, piperazine, morpholine, thiomorpholine or thiomorpholine S,S dioxide.

To enable them to manufacture the preferred compounds, the inventors may first manufacture an intermediate compound. The inventors believe that their method of manufacturing the intermediate compound is also novel.

In accordance with an eighth aspect, there is provided a method of manufacturing a compound of Formula (IV):

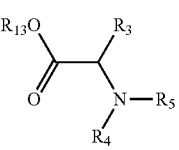

Formula (IV)

wherein $R_3$, $R_4$ and $R_5$ are as defined above and $R_{13}$ is H or a $C_{1-5}$ straight or branched alkyl or alkenyl; the method comprising contacting a compound of formula (V):

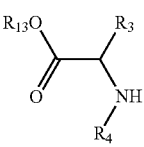

Formula (V)

with a benzene, a pyridine or a pyrimidine substituted with a leaving group and optionally substituted with one or more further substituents, wherein the or each further substituent is independently a $C_{1-5}$ straight or branched alkyl or alkenyl, a halogen, $SR_6$, $SO_2R_6$, $OR_6$, or $NR_6R_7$ and $R_6$ and $R_7$ are as defined above; characterised in that the reaction is conducted in a sealed vessel.

Advantageously, the sealed vessel prevents the benzene, pyridine or pyrimidine from escaping to the atmosphere.

Preferably, $R_{13}$ is a $C_{1-5}$ straight or branched alkyl or alkenyl. It will be understood that $R_{13}$ may be a methyl group, an ethyl group, a propyl group, a butyl group or a pentyl group. In one preferred embodiment, $R_{13}$ is a methyl group.

The leaving group may be any halogen, such as fluorine, chlorine, bromine or iodine. Preferably, $X_4$ is fluorine.

Preferably, the benzene, pyridine or pyrimidine is selected from the group consisting of:

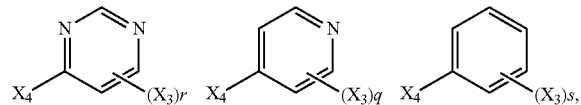

wherein $X_3$, r, q and s are as defined above, and $X_4$ is the leaving group.

Preferably, the method comprising contacting the compound of formula (V) with the pyridine or pyrimidine. More preferably, the method comprising contacting the compound of formula (V) with the pyridine.

Preferably, the pyridine comprises:

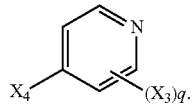

Most preferably, the pyridine is pentafluoropyridine.

Preferably, the compound of Formula (V) and the benzene, pyridine or pyrimidine are contacted in the presence of a base. Preferably, the base is trimethylamine.

The reaction may be carried out in a solution comprising dimethyl formamide (DMF), tetrahydrofuran (THF) and/or acetonitrile. Preferably, the reaction is carried out in a solution comprising dimethyl formamide.

Preferably, the solution is stirred for between 1 minute and 180 minutes. More preferably, the solution is stirred for between 5 minutes and 120 minutes, or between 10 minutes and 60 minutes. Most preferably, the solution is stirred for between 20 minutes and 40 minutes.

Preferably, the solution is stirred at a temperature between 0° C. and 50° C. More preferably, the solution is stirred at a temperature between 5° C. and 40° C. or between 10° C. and 30° C. Most preferably, the solution is stirred at about room temperature.

The method may comprise subsequently contacting the resultant compound with a metal hydroxide.

Advantageously, the method may produce a compound of Formula (IIIb) or (IIIc).

The metal hydroxide may comprise an alkali metal hydroxide, such as lithium hydroxide, sodium hydroxide or potassium hydroxide. Preferably the metal hydroxide comprises lithium hydroxide.

The step of subsequently contacting the resultant compound with a metal hydroxide may be carried out in an aqueous solution.

Preferably, the aqueous solution is stirred for at least 1 hour. More preferably, the solution is stirred for at least 2, 3, 4 or 5 hours. Most preferably, the solution is stirred for at least 10 or 15 hours.

Preferably, the aqueous solution is stirred at a temperature between 0° C. and 50° C. More preferably, the aqueous solution is stirred at a temperature between 5° C. and 40° C. or between 10° C. and 30° C. Most preferably, the aqueous solution is stirred at about room temperature.

The aqueous solution may be quenched with an acid. The acid is preferably hydrogen chloride.

In a further aspect, there is provided a compound of formula (I):

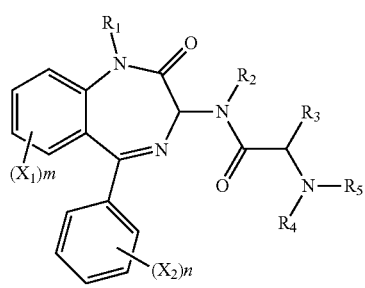

Formula (I)

wherein $R_1$ is H or a $C_{1-5}$ straight or branched alkyl or alkenyl;
$R_2$ is H or a $C_{1-5}$ straight or branched alkyl or alkenyl;
$R_3$ is any amino acid side chain; and $R_4$ is H or a $C_{1-5}$ straight or branched alkyl or alkenyl; or $R_3$ and $R_4$, together with the atoms to which they are attached, combine to form a five-membered heterocyclic ring;
$R_5$ is a six membered ring optionally substituted with one or more substituents, wherein the or each substituent is independently a $C_{1-5}$ straight or branched alkyl or alkenyl, a halogen, $SR_6$, $SO_2R_6$, $OR_6$, or $NR_6R_7$;
m is 0, 1, 2, 3 or 4;
n is 0, 1, 2, 3, 4 or 5;
the or each $X_1$ is independently selected from a $C_{1-5}$ straight or branched alkyl or alkenyl, a halogen, $SR_6$, $SO_2R_6$, $OR_6$ or $NR_6R_7$;
the or each $X_2$ is independently selected from a $C_{1-5}$ straight or branched alkyl or alkenyl, a halogen, $SR_6$, $SO_2R_6$, $OR_6$ or $NR_6R_7$;
the or each $R_6$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

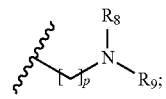

the or each $R_7$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

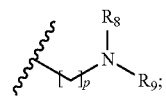

and/or $R_6$ and $R_7$ together with the nitrogen atom to which they are attached independently form a 3-7 membered ring;
p is 1, 2, 3, 4 or 5; and
$R_8$ and $R_9$ together with the nitrogen atom to which they are attached independently form a 3-7 membered ring;
or a pharmaceutically acceptable salt, solvate, tautomeric form or polymorphic form thereof.

All features described herein (including any accompanying drawings, claims and abstract), and/or all of the steps of any method or process so disclosed, may be combined with any of the above aspects in any combination, except combinations where at least some of such features and/or steps are mutually exclusive.

FIG. 1 shows the structure of N-{(3S)-2-oxo-5-phenyl-2,3-dihydro-1H-1,4-benzodiazepin-3-yl](tetrafluoropyridin-4-ylamino) acetamide.

EXAMPLES

Example 1: Synthesis of Compounds

Melting points were determined in open capillaries, using a Stuart SMP30 digital melting point apparatus and are uncorrected. NMR spectra were recorded on a Bruker Avance-III-400 (1H=400.06 MHz; 19F=376.4 MHz; 13C=100.6 MHz) at ambient probe temperature (nominal 295K) using either deuterated chloroform (CDCl$_3$) or hexadeuterated dimethylsulphoxide (DMSO-d6) as solvents. Chemical shifts (δ) are given in ppm vs. TMS ($^1$H NMR, $^{13}$C NMR) as an internal reference. Coupling constants are given in Hertz (Hz). LC ES MS (positive ion) was performed on a QToF Premier mass spectrometer equipped with an Acquity UPLC (Waters Corp.). The LC separation was achieved on a C18 BEH chromatography column (2.1 mm×100 mm and 1.7 um particle size) using a reverse phase gradient of 100% aqueous (0.1% formic acid in water) to 100% organic (0.1% formic acid in acetonitrile) at 0.6 mL/min. Silica gel plates, Supelco. S-A (Fluorescence Indicator at 254 nM) (Sigma-Aldrich Chemie GmbH Riedstr. 2D-8955T, Steinheim 497329-970, Germany) were used for TLC testing. Column chromatography was performed using silica gel (70-230 mesh) from Sigma-Aldrich (The Old Brickyard, Gillingham, SP8 4JL. UK). Reagents were also obtained from Sigma-Aldrich and used without further purification.

Intermediate 1: Methyl 2-[[tetrafluoropyridin-4-yl)amino]acetate

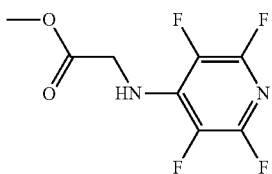

Pentafluoropyridine (0.4 ml) in DMF (2 ml) was treated with triethylamine (0.5 ml) and glycine methyl ester hydrochloride (250 mg) in a sealed vessel at room temperature and stirred there for 30 minutes. The mixture was partitioned between water and EtOAc. The layers were separated and the EtOAc layer washed with water (5×), a portion of brine, dried over sodium sulphate, decanted and concentrated in vacuo. The resulting solid was triturated with hexane to provide the title compound as a white solid. Yield: 0.221 g (87%); m.pt. 67-69° C.; $^1$H NMR (400 MHz, CDCl$_3$): =5.22 (bs, 1H, NH), 4.32 (bt, 2H, CH$_2$), 3.90 (s, 3H, OCH$_3$); $^{19}$F (376 MHz, CDCl$_3$)−93.61 (m, 2F), −163.97 (m, 2F).

Intermediate 2: 2-[(tetrafluoropyridin-4-yl)amino]acetic acid

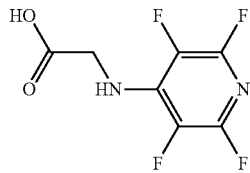 [SMILES: O=C(O)CNc1c(F)c(F)nc(F)c1F]

Methyl 2-[(tetrafluoropyridin-4-yl)amino]acetate (intermediate 1) (119 mg) in THF (9 ml) was treated with lithium hydroxide (164 mg) in water (9 ml) at room temperature. After 18 hours, 9 ml of 3M HCl was added followed by salt to saturation. This mixture was extracted with ethyl acetate (3 times), the combined extracts were dried over sodium sulphate before being decanted and concentrated in vacuo.

Compound 1: N-{(3S)-2-oxo-5-phenyl-2,3-dihydro-1H-1,4-benzodiazepin-3-yl](phenylamino)acetamide

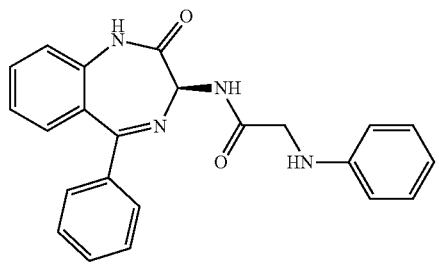 [SMILES: O=C(CNc1ccccc1)N[C@H]1N=C(c2ccccc2)c2ccccc2NC1=O]

(3S)-2-Oxo-5-phenyl-2,3-dihydro-1H-1,4-benzodiazepin-3-ylamine (126 mg) was combined with triethylamine (190 ul), HBTU (190 mg), N-phenylglycine (76 mg) in DMF (2.5 ml) and stirred at room temperature for 18 hours. Water (5 ml) was added and the resulting solid filtered. Chromatography on silica (200:8:1, DCM, ethanol, ammonia) provided the desired compound as a pale cream solid. Yield: 0.045 g (23%); $^1$H NMR (400 MHz, CDCl$_3$): δ=10.92 (s, 1H, NH), 8.94 (d, 1H, C(=O)NH), 7.66 (m, 1H, ArH), 7.54-7.43 (m, 5H, ArH), 7.10 (m, 2H, ArH), 6.60 (d, 2H, ArH), 6.50 (m, 1H, ArH), 6.06 (t, 1H, CH$_2$NHAr), 5.26 (d, 1H, C=NCH(C=O)N), 3.84 (2H, m, CH$_2$C=O)). $^{13}$C NMR (100 MHz, CDCl$_3$): δ=171.2, 168.1, 167.3, 148.8, 139.1, 138.5, 132.6, 131.1, 130.9, 129.9, 129.3, 128.8, 126.6, 123.8, 122.0, 117.1, 113.0, 56.5, 47-3);

Compound 2: N-{(3S)-2-oxo-5-phenyl-2,3-dihydro-1H-1,4-benzodiazepin-3-yl](tetrafluoropyridin-4-ylamino) acetamide

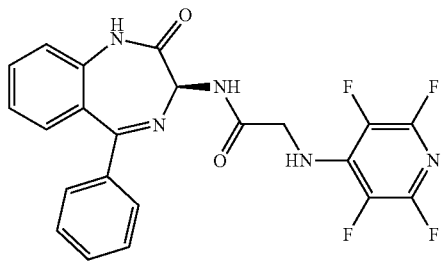 [SMILES: O=C(CNc1c(F)c(F)nc(F)c1F)N[C@H]1N=C(c2ccccc2)c2ccccc2NC1=O]

The above compound was prepared in an analogous manner to compound 1, substituting N-phenylglycine with 2-[(tetrafluoropyridin-4-yl)amino]acetic acid (intermediate 2). Yield: 0.11 g (48%); $^1$H NMR (400 MHz, CDCl$_3$): δ=9.43 (s, 1H, CONH), 8.25 (d, 1H, CHNHC=O) 7.51 (m, 3H, ArH), 7.44 (m, 1H, ArH), 7.36 (m, 3H, ArH), 7.22 (m, 2H, ArH), 5.65 (d, 1H, C=NCH(C=O)N), 5.55 (m, 1H, CH$_2$NHAr), 4.38 (2H, m, NHCH$_2$C=O). $^{13}$C NMR (100 MHz, CDCl$_3$): δ=168.9, 168.7, 168.5, 145.2, 142.8, 138.2, 137.3, 137.0, 132.5, 132.47, 131.5, 130.9, 130.0, 129.8, 128.3, 127.5, 124.4, 121.6, 67.6: $^{19}$F (376 MHz, CDCl$_3$)− 94.07 (m, 1F), −163.77 (m, 1F).

Compound 3: N-{2-oxo-5-phenyl-2,3-dihydro-1H-1,4-benzodiazepin-3-yl](phenylamino) acetamide

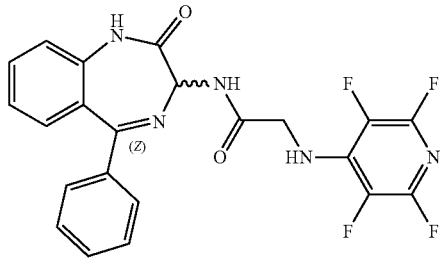 [SMILES: O=C(CNc1c(F)c(F)nc(F)c1F)NC1N=C(c2ccccc2)c2ccccc2NC1=O]

The above compound was prepared in an analogous manner to compound 1, substituting N-phenylglycine with 2-[(tetrafluoropyridin-4-yl)amino]acetic acid (Intermediate 2) and (3S)-2-oxo-5-phenyl-2,3-dihydro-H-1,4-benzodiazepin-3-ylamine with the racemate thereof. $^1$H NMR (400

MHz, CDCl₃): δ=10.90 (s, 1H, CONH), 9.34 (d, 1H, CHNHC=O) 7.65 (d, 1H, ArH), 7.55 (m, 5H, ArH), 7.48 (m, 3H, ArH)), 5.25 (d, 1H, C=NCH(C=O)N), 4.25 (2H, m, NHCH₂C=O). ¹³C NMR (100 MHz, CDCl₃): δ=168.9, 168.7, 168.5, 145.2, 142.8, 138.2, 137.3, 137.0, 132.5, 132.47, 131.5, 130.9, 130.0, 129.8, 128.3, 127.5, 124.4, 121.6, 67.6:19F (376 MHz, CDCl₃)–97.0 (m, 1F), –163.54 (m, 1F).

Compound 4: 2-[(2-ethoxy-3,5,6-trifluoropyridin-4-yl)amino]-N-{(3S)-2-oxo-5-phenyl-2,3-dihydro-1H-1,4-benzodiazepin-3-yl]acetamide

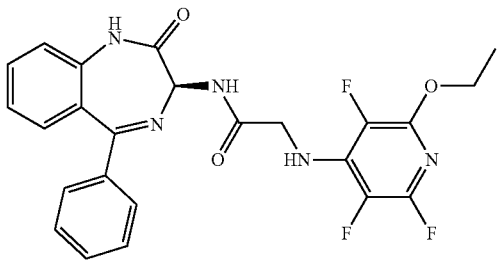 [SMILES: CCOc1nc(F)c(F)c(NCC(=O)N[C@H]2N=C(c3ccccc3)c3ccccc3NC2=O)c1F]

N-{(3S)-2-oxo-5-phenyl-2,3-dihydro-1H-1,4-benzodiazepin-3-yl](tetrafluoropyridin-4-ylamino) acetamide (Compound 2) (100 mg) was dissolved in ethanol (2 ml) and treated with sodium ethoxide (135 ul) at room temperature. The mixture was heated to 76° C. After 12 hours at this temperature the mixture was cooled to room temperature and a further portion (135 ul) of sodium ethoxide was added. The mixture was heated to 76° C. for a further 18 hours. Dilute HCl (2N, 3 ml) was added and the mixture partitioned between ethyl acetate and water. The aqueous phase was extracted with ethyl acetate (3×50 ml) and combined extracts were dried over sodium sulphate before being decanted and concentrated in vacuo. Chromatography on silica (150:8:1; CH₂Cl₂:EtOH:NH₄OH) gave isolation of the desired compound as a pale tan solid. Yield 0.04 g, (39%). ¹H NMR (400 MHz, CDCl₃): δ=10.90 (s, 1H, CONH), 9.34 (d, 1H, CHNHC=O) 7.65 (d, 1H, ArH), 7.55 (m, 5H, ArH), 7.48 (m, 3H, ArH)), 5.25 (d, 1H, C=NCH(C=O)N), 4.25 (2H, m, NHCH₂C=O). ¹³C NMR (100 MHz, CDCl₃): δ=168.9, 168.7, 168.5, 145.2, 142.8, 138.2, 137.3, 137.0, 132.5, 132.47, 131.5, 130.9, 130.0, 129.8, 128.3, 127.5, 124.4, 121.6, 67.6: ¹⁹F (376 MHz, CDCl₃) –97.0 (m, 1F), –163.54 (m, 1F):

Example 2: Antiviral and Cell Toxicity Assays

Cells were obtained from ATCC and the virus preparation was subjected to one round of centrifugation through a 40% (V/V) glycerol to remove any interferon produced from infected cells. Growth medium was Dulbecco's modified Eagle's medium (DMEM) with 10% (v/v) foetal calf serum (FCS), Viral maintainance medium was DMEM+2% (v/v) FCS.

Cytopathic Effect (CPE) Assay—IC50:
A549 cells and HeLa cells were used to seed a set of 96 well plates grown until 50% confluent, a 2 fold serial dilution of the compound was performed on each cell line with DMSO (only) as control starting with 100 μM of the compound. Medium used was DMEM+2% FCS (normal medium for viral growth).

Cells were allowed to grow for 6-8 days to mimic a TCID50 assay after which cell viability was determined by adding Almar blur (similar to XT) and reading at 600 nm (excitation 540 nm). The results obtained are shown in table 1.

TABLE 1

Results of cytopathic effect (CPE) assay

| Compound | CPE IC50 (μM) |
|---|---|
| 1 | 2.5 |
| 2 | 0.625 |
| 4 | 2.5 |

The results show that all three compounds are effective at treating at treating RSV. Due to the low IC50 value, compound 2 is the most effect compound at treating RSV. The fact that compound 2 is substantially more effective at treating RSV than compound 4 (the racemate) indicates that there is a chiral preference, and that therefore the compounds bind directly to a protein site within the virus.

Cell Cytotoxicity—CC50 (Concentration at which 50% Cell Toxicity is Observed):

A549 cells and HeLa cells were used to seed a set of 96 well plates grown until 50% confluent, a 2 fold serial dilution of the compound was performed on each cell line with DMSO (only) as control starting with 100 μM of the compound. Medium used was DMEM+2% FCS (normal medium for viral growth).

Cells were allowed to grow for 6-8 days to mimic a TCID50 assay after which cell viability was determined by adding Almar blur (similar to XT) and reading at 600 nm (excitation 540 nm).

The results obtained are shown in table 2.

TABLE 2

Results of cell cytotoxicity assay

| Compound | CC50 (μM) |
|---|---|
| 1 | 25 |
| 2 | 100 |
| 4 | >100 |

CC50 for all three of the compounds was significantly higher than the CPE IC50 value. This suggests that the compounds are not toxic at concentrations which may be used to treat RSV.

Plaque Reduction Assay

Vero cells were seeded in 96-well plates in a volume of 100 μL of Optimem supplemented with 3% FCS at a concentration of 4×10⁴ cells per well. After an overnight incubation at 37° C. in a humidified 5% CO₂ atmosphere, the monolayer of cells should be approximately 90% confluent. Compound 2 was titrated in pre-warmed Serum Free (SF) Optimem in a U-bottom 96 well plate. For compounds in a DMSO solution, titration in 100% DMSO was performed first and each concentration added individually to a 2× final concentration at 4% DMSO in SF media before mixing with virus (2% final DMSO with virus). Media was then removed from cells and replaced with PBS (100~l/well). RSV stock was thawed and diluted in SF Optimem media to 4000 PFU/mLl. An equal volume of virus was added to compounds on the titration plate. PBS was removed from cells which were then inoculated with the virus/compound solution (50 μL/well). Cells were incubated for 2 h in a 37°

C.+5% $CO_2$ humidified incubator to allow infection. Inoculum was removed and media (Optimem+1% FCS) added to cells (100 l/well). Cells were subsequently incubated for 48 h at 37° C.+5% $CO_2$ in a humidified incubator.

Immunostaining Procedure:

Media was removed from cells and the monolayer washed with PBS. Cells were fixed with ice cold 80% Acetone in PBS (100 l/well) for 20 mins at −20° C. Fixative was removed and cells are dried for 30 mins with plates inverted. Blocking solution (5% skim milk powder in PBS-T) was added to cells (150 µL/well) and plates were incubated for 30 mins at room temperature. Blocking solution was removed and plates washed once with PBS-T. Primary antibody in blocking solution was added to plates (50l/well) and incubated for 1 h at 37° C. Plates were then washed 3 times with PBS-T. Secondary antibody in blocking solution was added to plates (50 µL/well) and incubated for 1 h at 37° C. in the dark. Plates were washed as above and then dried for 10 mins. Plates were scanned on the Odyssey Imager (Li-Cor Biosciences) at a resolution of 42 µM, medium quality and level 5 intensity in the 800 nM channel.

Data Analysis:

Images obtained were saved and plaque numbers counted with the aid of computer imaging software. $IC_{50}$ values for compounds were derived from dose response curves [three variable log(inhibitor) vs response] obtained using Graphpad Prism software.

The results are given in Table 3.

TABLE 3

Standard plaque reduction assay data and time of addition study plaque reduction assay data for compound 2

| Plaque IC50 µM | Plaque IC50 µM (during infection only) | Plaque IC50 µM (post infection only) |
|---|---|---|
| 1.1 | 10.9 | 2 |

The plaque reduction assay supports the data showing that the compound may be used to treat RSV. In addition to this standard plaque reduction assay, the compounds were tested against RSV in two further formats: first compounds were added during infection only and removed during the replication phase and in a second format the compounds were added only during the replication phase, post infection Since the IC50 value of the second plaque reduction is much higher than the standard plaque reduction assay this suggests that the compound is not effective in the first two hours of infection. Similarly, since the IC50 values for the standard and second format plaque reduction assays are similar, it strongly suggests that the compound acts relatively late in the viral life cycle. In turn, this suggests that the compound is a viral replication inhibitor. Although they do not wish to be bound by any hypothesis, the inventors believe that the compound of the invention bind to the N-protein of RSV, and so inhibits virus replication, and is unlikely to be viral-host cell fusion inhibitors, which may have been the case had the compounds acted earlier in the viral life cycle.

Cytotoxicity

MTT Cell Toxicity Assay

Vero cells were seeded in 96-well plates in a volume of 100 µL Optimem media supplemented with 1% FBS at a concentration of 1×10⁴ cells per well. After an overnight incubation at 37° C. in a humidified 5% $CO_2$ atmosphere, the monolayer of cells should be approximately 90% confluent. Compound 2 was titrated in pre-warmed Serum Free (SF) Optimem in a U-bottom 96 well plate. For compounds in a DMSO solution, titration in 100% DMSO was performed first and each concentration added individually to a 2× final concentration at 4% DMSO. Media was then removed from cells and replaced with titrated compounds (100 µl/well). Cells were incubated at 37° C. in a humidified 5% $CO_2$ atmosphere for 48 hours.

The MTT solution on Optimem (4 mg/ml) was prepared and 2 ul added to each well before it was incubated for 2 hours at 37° C. in a humidified 5% $CO_2$ atmosphere. Media was then removed from the cells and DMSO added (50 ul/well). Plates were placed on a shaker prior to reading in a Spectromax at 570 nm. Data was normalised relative to untreated controls (1% DMSO only) and CC50 values determined using non-linear regression analysis with Graphpad Prism software.

Using this method compound 2 was found to have a CC50 value of 63 µM. The difference in cytotoxicity values observed for compound 2 may be due to a cell line difference (Vero versus A549) coupled with biological variability. It should also be noted that the different experiments were performed in different labs at different times, which could also lead to a degree of variability.

Meanwhile, a CC50 value of 63 µM is still significantly higher than the CPE IC50 value. This further supports the conclusion that compound 2 is not toxic at concentrations which may be used to treat RSV.

Results and Discussion

The results show that compounds 1, 2 and 4 may be used to treat RSV. Furthermore, the compounds are effective at non-toxic concentrations. It is thought that the compounds bind directly to a protein site and inhibits replication of the virus.

Example 3: Permeability Assays

MDR1-MDCK cells obtained from the NIH (Rockville, Md., USA) are used between passage numbers 6-30. Cells are seeded onto Millipore Multiscreen Transwell plates at 3.4×10⁵ cells/cm². The cells are cultured in DMEM and media is changed on day 3. On day 4 the permeability study is performed. Cell culture and assay incubations are carried out at 37° C. in an atmosphere of 5% CO2 with a relative humidity of 95%. On the day of the assay, the monolayers are prepared by rinsing both basolateral and apical surfaces twice with Hanks Balanced Salt Solution (HBSS) at the desired pH warmed to 37° C. Cells are then incubated with HBSS at the desired pH in both apical and basolateral compartments for 40 min to stabilise physiological parameters.

The dosing solutions are prepared by diluting compound 2 with assay buffer to give a final compound 2 concentration of 10 µM (final DMSO concentration of 1% v/v). The fluorescent integrity marker lucifer yellow is also included in the dosing solution. Analytical standards are prepared from test compound DMSO dilutions and transferred to buffer, maintaining a 1% v/v DMSO concentration.

For assessment of A-B permeability, HBSS is removed from the apical compartment and replaced with compound 2 dosing solution. The apical compartment insert is then placed into a companion plate containing fresh buffer (containing 1% v/v DMSO). For assessment of B-A permeability, HBSS is removed from the companion plate and replaced with compound 2 dosing solution. Fresh buffer (containing 1% v/v DMSO) is added to the apical compartment insert, which is then placed into the companion plate.

At 60 min the apical compartment inserts and the companion plates are separated and apical and basolateral samples diluted for analysis.

Compound 2 permeability is assessed in duplicate. Compounds of known permeability characteristics are run as controls on each assay plate.

Compound 2 and control compounds are quantified by LC-MS/MS cassette analysis using an 8-point calibration with appropriate dilution of the samples. The starting concentration ($C_o$) is determined from the dosing solution and the experimental recovery calculated from $C_o$ and both apical and basolateral compartment concentrations.

The integrity of the monolayer throughout the experiment is checked by monitoring lucifer yellow permeation using fluorimetric analysis. Lucifer yellow permeation is high if monolayers have been damaged.

The permeability data is shown in Table 4.

TABLE 4

Permeability data for compound 2

| Permeability A2B (cm/s) | Permeability B2A (cm/s) | Efflux ratio B2A/A2B |
|---|---|---|
| 0.553 | 76.3 | 138 |

This data indicates that compound 2 is a permeable compound but with a susceptibility for an efflux mechanism, possibly via a transporter such as PGP.

Example 4: Clearance Assays

Pooled human liver microsomes (pooled male and female), pooled rat liver microsomes (male Sprague Dawley rats) and pooled dog liver microsomes (male Beagle dog) are purchased from a reputable commercial supplier and stored at −80° C. prior to use.

Microsomes (final protein concentration 0.5 mg/mL), 0.1 M phosphate buffer pH 7.4 and compound 2 (final substrate concentration 3 µM; final DMSO concentration 0.25%) are pre-incubated at 37° C. prior to the addition of NADPH (final concentration 1 mM) to initiate the reaction. The final incubation volume is 50 µL. A control incubation is included for each compound tested where 0.1 M phosphate buffer pH 7.4 is added instead of NADPH (minus NADPH). Two control compounds are included with each species. All incubations are performed singularly for each test compound.

Compounds are incubated for 0, 5, 15, 30 and 45 min. The control (minus NADPH) is incubated for 45 min only. The reactions are stopped by transferring 25 µL of incubate to 50 µL methanol at the appropriate time points. The termination plates are centrifuged at 2,500 rpm for 20 min at 4° C. to precipitate the protein. Following protein precipitation, the sample supernatants are combined in cassettes of up to 4 compounds, internal standard is added and samples analysed by LC-MS/MS. From a plot of ln peak area ratio (compound peak area/internal standard peak area) against time, the gradient of the line is determined. Subsequently, half-life and intrinsic clearance are calculated, and this is shown in Table 5.

TABLE 5

Microsomal clearance data for compound 2

| Intrinsic clearance - rat (µl/min/mg) | t½ - rat (mins) | Intrinsic clearance - dog (µl/min/mg) | t½ - dog (mins) | Intrinsic clearance - human (µl/min/mg) | t½ - human (mins) |
|---|---|---|---|---|---|
| 29.2 | 47.5 | 7.05 | 197 | 52.6 | 26.3 |

This data indicates the potential of the example to undergo phase 1 metabolism. Moderate and low clearances are observed for the example in rat and dog microsomal preparations with a higher clearance observed in human microsomal preparations.

Example 5: Mouse In Vivo Pharmacokinetic Assay

Pharmacokinetic evaluation of compound 2 was performed in male CD-1 mice following intravenous (IV) and oral (PO) administration. For intravenous administration the compound was formulated in solution in 40:60 DMA:saline and was administered at 1 mg/kg via the tail vein. For oral administration the compound was formulated in suspension in water containing 1% methylcellulose and 0.1% Tween80, and was administered at 10 mg/kg by oral gavage. Blood samples were taken by cardiac puncture under terminal anaesthesia (isoflurane) at ten timepoints between 1 minute and 24 hours following IV administration, and at nine timepoints between 5 minutes and 24 hours following PO administration (n=3 per timepoint). Plasma was immediately obtained by centrifugation, and the resulting samples frozen until analysis. Samples, along with a calibration curve prepared by spiking the compound into control plasma, were subsequently prepared for quantitative analysis by precipitation of plasma proteins with acetonitrile. Analysis was by ultra high performance liquid chromatography (Agilent 1290 system) coupled to time of flight mass spectrometry, using electrospray ionisation (Agilent 6550 system). Pharmacokinetic parameters were determined by non-compartmental analysis of mean concentration data using Phoenix WinNonlin v6.4. The data obtained is shown in Table 6.

TABLE 6

In vivo mouse pharmacokinetic data for compound 2

| IV Clearance (ml/min/kg) | IV t½ (mins) | Vd (L/kg) | PO t½ (mins) | PO cmax (ng/ml) | F (%) |
|---|---|---|---|---|---|
| 63.1 | 59 | 3.65 | 132 | 349 | 54.8 |

This data indicates the example 2 is orally bioavailable with moderate clearance.

Example 6: Synthesis of Further Compounds

Reagents were obtained from commercial sources and were used without further purification. Anhydrous reactions were carried out in oven-dried glassware under a nitrogen atmosphere. TLC was performed on aluminium backed silica gel plates with fluorescence indicator at 254 nM (median pore size 60 Å). Flash column chromatography was performed using a Biotage Isolera One system using KP-Sil, Ultra or KP-NH columns. NMR spectra were recorded on a 400 MHz spectrometer at ambient probe temperature (nominal 295K). Chemical shifts (δ) are given in ppm and calibrated by using the residual peak of the solvent as the internal standard (CDCl$_3$, δ$_H$=7.26 ppm, δ$_C$=77.16 ppm; DMSO-d$_6$, δ$_H$=2.50 ppm, δ$_C$=39.52 ppm). Coupling constants are given in Hertz (Hz). LRMS were recorded using an Advion Plate Express expression$^L$ compact mass spectrometer equipped with either an APCI or ESI ion source.

Preparatory Examples

Intermediates

3A: tert-Butyl 2-[(2,3,5,6-tetrafluoropyridin-4-yl)amino]acetate

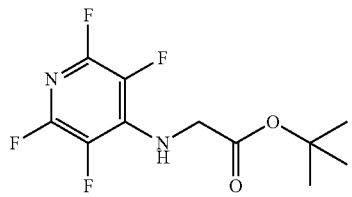 [SMILES: CC(C)(C)OC(=O)CNc1c(F)c(F)nc(F)c1F]

Pentafluoropyridine (3.293 mL, 30 mmol) was added to a cooled (0° C.) solution of glycine tert-butyl ester hydrochloride (2.514 g, 15 mmol) and triethylamine (4.39 mL, 31.5 mmol) in DMF (45 mL) and stirred at 0° C. for 6 h. The reaction was allowed to attain rt and stirred for 18 h. The volatiles were removed under reduced pressure and the residue purified by flash chromatography (SiO$_2$, 0-45% EtOAc in heptane) to afford a white solid. $^1$H NMR (400 MHz, CDCl$_3$): δ 5.16 (br s, 1H), 4.20-4.15 (m, 2H), 1.50 (s, 9H). LRMS (APCI−) m/z 278.6 [M−H]$^-$.

The following intermediate compounds were prepared by the same general procedure.

TABLE 7

Intermediate compounds of formula (3)

(3)

| Prep Example | R | Name | $^1$H NMR δ (400 MHz) | LRMS | TLC $R_f$ value |
|---|---|---|---|---|---|
| 3B | | tert-Butyl (2S)-2-[(2,3,5,6-tetrafluoropyridin-4-yl)amino]propanoate | (CDCl$_3$): δ 5.12 (br s, 1H), 4.52-4.43 (m, 1H), 1.52 (d, J = 7.0 Hz, 3H), 1.49 (s, 9H) | APCI− 292.7 [M − H]$^-$ | |
| 3C | | tert-Butyl (2R)-2-[(2,3,5,6-tetrafluoropyridin-4-yl)amino]propanoate | (CDCl$_3$): δ 5.12 (br s, 1H), 4.52-4.43 (m, 1H), 1.52 (d, J = 7.0 Hz, 3H), 1.48 (s, 9H) | APCI− 292.8 [M − H]$^-$ | |
| 3D | | tert-Butyl (2S)-3-methyl-2-[(2,3,5,6-tetrafluoropyridin-4-yl)amino]butanoate | (CDCl$_3$): δ 5.09 (d, J = 9.0 Hz, 1H), 4.38-4.32 (m, 1H), 2.27-2.17 (m, 1H), 1.49 (9H), 1.04 (d, J = 6.9 Hz, 3H), 1.01 (d, J = 6.9 Hz, 3H) | APCI+ 322.8 [M + H]$^+$ | |
| 3E | | tert-butyl (2R)-3-methyl-2-[(2,3,5,6-tetrafluoropyridin-4-yl)amino]butanoate | (CDCl$_3$): δ 5.09 (d, J = 9.0 Hz, 1H), 4.38-4.32 (m, 1H), 2.27-2.17 (m, 1H), 1.49 (9H), 1.04 (d, J = 7.0 Hz, 3H), 1.01 (d, J = 6.9 Hz, 3H) | APCI+ 322.8 [M + H]$^+$ | |
| 3F | | tert-butyl (2S)-3-phenyl-2-[(2,3,5,6-tetrafluoropyridin-4-yl)amino]propanoate | | APCI+ 371.1 [M + H]$^+$ | 0.69 (EtOAc: heptane; 1:2) |
| 3G | | tert-butyl (2S)-1-(2,3,5,6-tetrafluoropyridin-4-yl)pyrrolidine-2-carboxylate | (CDCl$_3$): δ 4.69-4.63 (m, 1H), 3.99-3.91 (m, 1H), 3.90-3.81 (m, 1H), 2.35-2.24 (m, 1H), 2.09-1.91 (m, 3H), 1.44 (s, 9H) | APCI+ 320.8 [M + H]$^+$ | |

TABLE 7-continued

Intermediate compounds of formula (3)

(3)

| Prep Example | R | Name | $^1$H NMR δ (400 MHz) | LRMS | TLC $R_f$ value |
|---|---|---|---|---|---|
| 3H | tert-butyl (2R)-pyrrolidine-2-carboxylate N-linked | tert-butyl (2R)-1-(2,3,5,6-tetrafluoropyridin-4-yl)pyrrolidine-2-carboxylate | (CDCl$_3$): δ 4.69-4.63 (m, 1H), 4.00-3.91 (m, 1H), 3.89-3.81 (m, 1H), 2.35-2.24 (m, 1H), 2.10-1.91 (m, 3H), 1.44 (s, 9H) | APCI+ 320.8 [M + H]$^+$ | |
| 3J | morpholine N-linked | 4-(2,3,5,6-Tetrafluoropyridin-4-yl)morpholine | (CDCl$_3$): δ 3.94-3.80 (m, 4H), 3.52-3.46 (m, 4H) | — | 0.55 (EtOAc: heptane; 1:2) |
| 3K | thiomorpholine N-linked | 4-(2,3,5,6-Tetrafluoropyridin-4-yl)thiomorpholine | (CDCl$_3$): δ 3.71-3.67 (m, 4H), 2.78-2.74 (m, 4H) | — | 0.4 (EtOAc: heptane; 1:9). |
| 3L | 1-acetylpiperazin-4-yl | 1-[4-(2,3,5,6-tetrafluoropyridin-4-yl)piperazin-1-yl]ethan-1-one | (CDCl$_3$): δ 3.80-3.58 (m, 4H), 3.53-3.43 (m, 4H), 2.16 (s, 3H) | APCI+ 278.0 [M + H]$^+$ | |
| 3M | N,N-diethylamino | N,N-Diethyl-2,3,5,6-tetrafluoropyridin-4-amine | (DMSO-d$_6$) δ 3.42 (qt, J = 7.0, 1.5 Hz, 4H), 1.17 (t, J = 7.0 Hz, 6H) | APCI+ 223.1 [M + H]+ | |
| 3N | 4,4-difluoropiperidin-1-yl | 4-(4,4-Difluoropiperidin-1-yl)-2,3,5,6-tetrafluoropyridine | (DMSO-d$_6$) δ 3.55 (t, J = 5.8 Hz, 4H), 2.18-2.04 (m, 4H). | — | 0.78 (EtOAc: heptane; 1:1) |

4A: Ethyl 2-{[3,5,6-trifluoro-4-(thiomorpholin-4-yl)pyridin-2-yl)amino}acetate

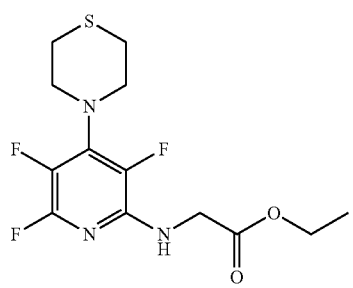 [SMILES: CCOC(=O)CNc1nc(F)c(F)c(N2CCSCC2)c1F]

A solution of 4-(2,3,5,6-tetrafluoropyridin-4-yl)thiomorpholine (intermediate 3K) (856 mg, 3.39 mmol), glycine ethyl ester hydrochloride (947 mg, 6.79 mmol) and K$_2$CO$_3$ (1.641 g, 11.88 mmol) in N-methyl-2-pyrrolidinone (NMP, 10 mL) was heated in a sealed tube at 100° C. for 17 h. After cooling to rt, the reaction was quenched with saturated aqueous NaHCO$_3$ solution (20 mL) and extracted with EtOAc (3×20 mL). The combined organic extracts were washed successively with saturated aqueous NaHCO$_3$ solution, water then brine (20 mL each), dried (Na$_2$SO$_4$) and the solvent removed under reduced pressure. Purification by flash chromatography (SiO$_2$, 0-30% EtOAc in heptane) afforded a white solid (541 mg, 48%0). $^1$HNMR (400 MHz, DMSO-d$_6$) δ: 7.11 (t, J=6.3 Hz, 1H), 4.09 (d, J=7.1 Hz, 2H), 3.92 (d, J=6.2 Hz, 2H), 3.54-3.48 (m, 4H), 2.72-2.67 (m, 4H), 1.17 (t, J=7.1 Hz, 3H). LRMS (APCI+) m/z 336.0 [M+H]$^+$.

The following intermediate compounds were prepared by the same general procedure.

TABLE 8

Intermediate compounds of formula (4)

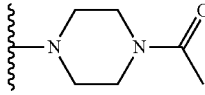

| Prep Ex | R | Name | LRMS APCI+ | TLC $R_f$ value |
|---|---|---|---|---|
| 4B | 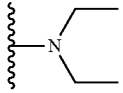 | Ethyl 2-{[4-(4-acetylpiperazin-1-yl)-3,5,6-trifluoropyridin-2-yl]amino}acetate | 361.1 [M + H]⁺ | 0.59 (EtOAc) |
| 4C |  | Ethyl 2-{[4-(diethylamino)-3,5,6-trifluoropyridin-2-yl]amino}acetate | 306.2 [M + H]⁺ | 0.77 (EtOAc: heptane; 1:1) |
| 4D | | Ethyl 2-{[4-(4,4-difluoropiperidin-1-yl)-3,5,6-trifluoropyridin-2-yl]amino}acetate | 354.1 [M + H]⁺ | 0.63 (EtOAc: heptane; 1:1) |

5-A: tert-Butyl 2-{[2,3,5-trifluoro-6-(morpholin-4-yl)pyridin-4-yl]amino}acetate 6A: tert-Butyl 2-{[2,3,5-trifluoro-6-(methylsulfanyl)pyridin-4-yl]amino}acetate

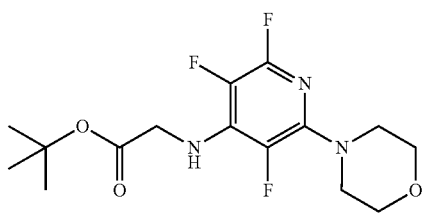 [SMILES: CC(C)(C)OC(=O)CNc1c(F)c(F)nc(N2CCOCC2)c1F]

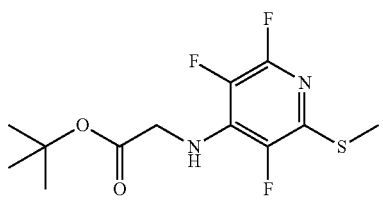 [SMILES: CSc1nc(F)c(F)c(NCC(=O)OC(C)(C)C)c1F]

A solution of tert-butyl 2-[(2,3,5,6-tetrafluoropyridin-4-yl)amino]acetate (intermediate 3A) (200 mg, 0.710 mmol) and morpholine (71.8 µL, 0.820 mmol) in DMF (4 mL) was heated at 80° C. for 7 h. Extra morpholine (15.6 µL, 0.178 mmol) was added and the reaction heated at 85° C. for a further 18 h. After cooling to rt, the reaction was diluted with water (15 mL) and extracted with EtOAc (3×15 mL). The combined organic extracts were washed successively with water (3×20 mL) and brine (20 mL), dried (MgSO₄) and the solvent removed under reduced pressure. Purification by flash chromatography (SiO₂, 3-50% EtOAc:heptane) afforded the product as a white solid (120 mg, 48%). ¹H NMR (400 MHz, CDCl₃): 4.84 (br s, 1H), 4.13-4.10 (m, 2H), 3.81-3.77 (m, 4H), 3.35-3.30 (m, 4H), 1.49 (s, 9H). LRMS (APCI+) m/z 347.8 [M+H]⁺.

Sodium methanethiolate (58 mg, 0.820 mmol) was added to a solution of tert-butyl 2-[(2,3,5,6-tetrafluoropyridin-4-yl)amino]acetate (intermediate 3A) (200 mg, 0.710 mmol) in DMF (4 mL) and heated at 80° C. for 7 h. The reaction mixture was cooled to rt, diluted with water (20 mL) and extracted with EtOAc (3×20 mL). The combined organic extracts were washed successively with water (4×30 mL) and brine (15 mL), dried (Na₂SO₄) and the solvent removed under reduced pressure. Purification by flash chromatography (SiO₂, 0-100% EtOAc:heptane) afforded the product as a yellow oil (182 mg, 83%). ¹H NMR (400 MHz, CDCl₃): δ 4.89 (s, 1H), 4.15-4.11 (m, 2H), 2.49 (s, 3H), 1.49 (s, 9H). LRMS (APCI+) m/z 308.8 [M+H]⁺

7A: tert-Butyl 2-[(2,3,5-trifluoro-6-methanesulfonylpyridin-4-yl)amino]acetate

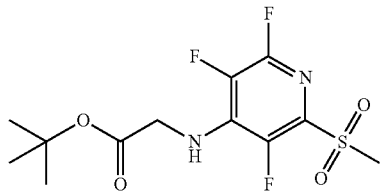 [SMILES: CC(C)(C)OC(=O)CNc1c(F)c(F)nc(S(C)(=O)=O)c1F]

meta-Chloroperoxybenzoic acid (m-CPBA) (~77% pure, 384 mg, 1.710 mmol) was added to a cooled (0° C.) solution of tert-butyl 2-[(2,3,5-trifluoro-6-methylsulfanylpyridin-4-yl)amino]acetate (intermediate 3A) (176. mg, 0.570 mmol) in $CH_2Cl_2$ (5 mL) and stirred for 3 h. The reaction was diluted with saturated aqueous $NaHCO_3$ solution (15 mL) and extracted with $CH_2Cl_2$ (3×20 mL). The combined organic extracts were washed successively with NaOH (0.5 M aqueous solution), saturated aqueous $NaHCO_3$ solution (2×) and brine (20 mL each), dried ($Na_2SO_4$) and the solvent removed under reduced pressure. Purification by flash chromatography ($SiO_2$, 0-70% EtOAc in heptane) gave the product as a white solid (149 mg, 76%). $^1$H NMR (400 MHz, $CDCl_3$): 5.31 (br s, 1H), 4.22-4.18 (m, 2H), 3.26 (s, 3H), 1.51 (s, 9H). LRMS (APCI−) m/z 338.7 [M−H]⁻.

8A: Ethyl 2-{[3,5,6-trifluoro-4-(morpholin-4-yl]pyridin-2-yl]amino}acetate

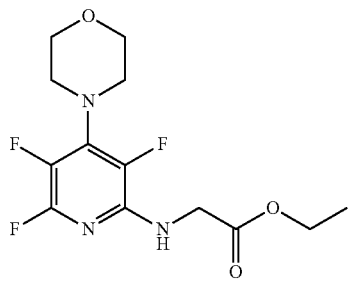 [SMILES: CCOC(=O)CNc1nc(F)c(F)c(N2CCOCC2)c1F]

A solution of 4-(2,3,5,6-tetrafluoropyridin-4-yl)morpholine (intermediate 3J) (180 mg, 0.760 mmol), ethyl 2-aminoacetate hydrochloride (128 mg, 0.910 mmol) and $K_2CO_3$ (253 mg, 1.830 mmol) in DMF (2.5 mL) was heated at 60° C. for 4 h, then at 100° C. for 44 h. The reaction mixture was cooled to rt, diluted with water (20 mL) and extracted with EtOAc (3×15 mL). The combined organic extracts were washed successively with water (4×15 mL) and brine (15 mL), dried ($Na_2SO_4$) and the solvent removed under reduced pressure. Purification by flash chromatography (0-100% EtOAc in heptane) afforded the product as a white solid (84 mg, 34%). $^1$H NMR (400 MHz, $CDCl_3$) δ 4.88 (br s, 1H), 4.23 (q, J=7.1 Hz, 2H), 4.12 (d, J=5.6 Hz, 2H), 3.82-3.77 (m, 4H), 3.41-3.36 (m, 4H), 1.29 (t, J=7.1 Hz, 2H). LRMS (APCI+) m/z 319.8 [M+H]⁺

9A: (2S)-2-[(2,3,5,6-Tetrafluoropyridin-4-yl)amino]propanoic acid

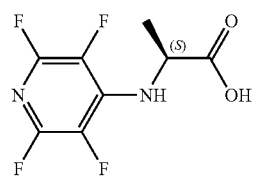

A solution of tert-butyl (2S)-2-[(2,3,5,6-tetrafluoropyridin-4-yl)amino]propanoate (intermediate 3B) (212 mg, 0.720 mmol) was stirred in $CH_2Cl_2$/trifluoroacetic acid (TFA; 1:1, 2 mL) at rt for 4 h. The volatiles were removed under reduced pressure to afford the crude product as a white solid (171 mg, 99.5%). $^1$H NMR (400 MHz, $CDCl_3$): δ 4.98 (d, J=6.9 Hz, 1H), 4.74-4.65 (m, 1H), 1.64 (d, J=7.1 Hz, 3H). LRMS (APCI−) m/z 236.9 [M−H]⁻.

The following intermediate compounds were prepared by the same general procedure.

TABLE 8

Intermediate compounds of formula (9)

(9)

| Prep Ex | R | Name | $^1$H NMR δ (400 MHz) | LRMS | TLC $R_f$ value |
|---|---|---|---|---|---|
| 9B |  | (2R)-2-[(2,3,5,6-Tetrafluoropyridin-4-yl)amino]propanoic acid | ($CDCl_3$): δ 4.98 (d, J = 7.5 Hz, 1H), 4.74-4.65 (m, 1H), 1.64 (d, J = 7.1 Hz, 3H) | APCI− 236.7 [M − H]⁻ |  |

TABLE 8-continued

Intermediate compounds of formula (9)

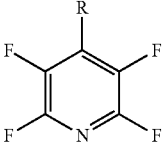

| Prep Ex | R | Name | $^1$H NMR δ (400 MHz) | LRMS | TLC $R_f$ value |
|---|---|---|---|---|---|
| 9C | 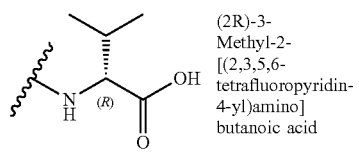 | (2S)-3-Methyl-2-[(2,3,5,6-tetrafluoropyridin-4-yl)amino]butanoic acid | (CDCl$_3$): δ 4.96 (d, J = 9.4 Hz, 1H), 4.57-4.51 (m, 1H), 2.38-2.27 (m, 1H), 1.11-1.06 (m, 6H). | APCI+ 266.8 [M + H]$^+$ | |
| 9D | 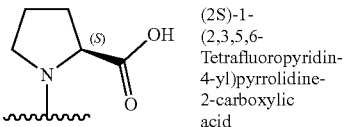 | (2R)-3-Methyl-2-[(2,3,5,6-tetrafluoropyridin-4-yl)amino]butanoic acid | (CDCl$_3$): δ 4.95 (d, J = 9.4 Hz, 1H), 4.56-4.52 (m, 1H), 2.39-2.26 (m, 1H), 1.11-1.06 (m, 6H). | APCI− 264.7 [M − H]$^−$ | |
| 9E | 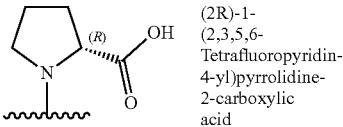 | (2S)-1-(2,3,5,6-Tetrafluoropyridin-4-yl)pyrrolidine-2-carboxylic acid | (CDCl$_3$): δ 4.88-4.82 (m, 1H), 4.03-3.93 (m, 1H), 3.92-3.83 (m, 1H), 2.24-2.15 (m, 1H), 2.29-2.15 (m, 1H), 2.11-1.95 (m, 2H). | APCI+ 264.8 [M + H]$^+$ | |
| 9F | 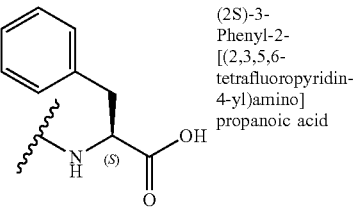 | (2R)-1-(2,3,5,6-Tetrafluoropyridin-4-yl)pyrrolidine-2-carboxylic acid | (CDCl$_3$): δ 4.88-4.82 (m, 1H), 4.03-3.94 (m, 1H), 3.92-3.83 (m, 1H), 2.44-2.33 (m, 1H), 2.24-2.15 (m, 1H), 2.10-1.97 (m, 2H). | APCI+ 264.8 [M + H]$^+$ | |
| 9G |  | (2S)-3-Phenyl-2-[(2,3,5,6-tetrafluoropyridin-4-yl)amino]propanoic acid | (DMSO-d$_6$) δ 13.25 (s, 1H), 7.49-7.45 (m, 2H), 7.43-7.32 (m, 3H), 7.28 (d, J = 7.3 Hz, 1H), 5.58 (d, J = 7.2 Hz, 1H), 3.65-3.40 (m, 2H) | | 0.51 (EtOAc: heptane; 1:2) |

10A: 2-[(2,3,5-Trifluoro-6-methanesulfonylpyidin-4-yl)amino]acetic acid

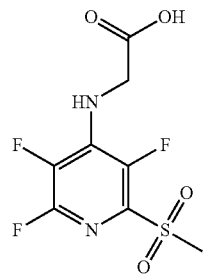 [SMILES: CS(=O)(=O)c1nc(F)c(F)c(NCC(=O)O)c1F]

Prepared by the general procedure described for intermediate 9A from intermediate 7A. $R_f$=0.17 (EtOAc).

11A: 2-{[2,3,5-Trifluoro-6-(morpholin-4-yl)pyridin-4-yl]amino}acetic acid hydrochloride

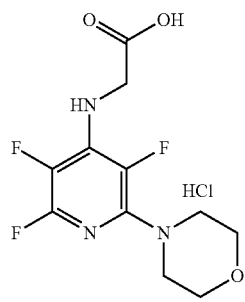

tert-Butyl 2-{[2,3,5-trifluoro-6-(morpholin-4-yl)pyridin-4-yl]amino}acetate (intermediate 5A) (119 mg, 0.340 mmol) was suspended in a mixture of HCl (1 M aqueous) and Et$_2$O (1:1, 6 mL) and stirred at rt for 24 h. Further HCl (2 M in Et$_2$O, 3 mL) was added and the reaction stirred for 24 h. The volatiles were removed under reduced pressure to afford the crude product as a pale brown solid (97 mg, 86%). $R_f$=0.66 (EtOAc). LRMS (APCI+) m/z 292.2 [M+H]$^+$

12A: Lithium (2-{[3,5,6-trifluoro-4-(morpholin-4-yl)pyridin-2-yl]amino}acetate

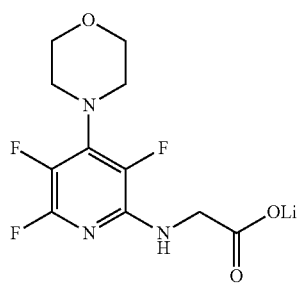

LiOH (1 M aqueous, 392 µL, 0.392 mmol) was added to a solution of ethyl 2-[(3,5,6-trifluoro-4-morpholin-4-ylpyridin-2-yl)amino]acetate (intermediate 8A) (63 mg, 0.200 mmol) in THF (2.5 mL) and stirred at rt for 20 h. The volatiles were removed under reduced pressure and the residue triturated with Et$_2$O. The residue was then dissolved in CH$_2$Cl$_2$:iPrOH:EtOH (~4:1:1), filtered, washing with EtOH and the solvent removed under reduced pressure to afford the crude lithium salt as a white solid. $^1$H NMR (400 MHz, DMSO-d$_6$): δ 5.92 (br s, 1H), 3.70-3.65 (m, 2H), 3.42-3.26 (m, 8H). LRMS (APCI+) m/z 291.7 [M+H]$^+$

13A: 2-{[4-(4-Acetylpiperazin-1-yl)-3,5,6-trifluoropyridin-2-yl]amino}acetic acid

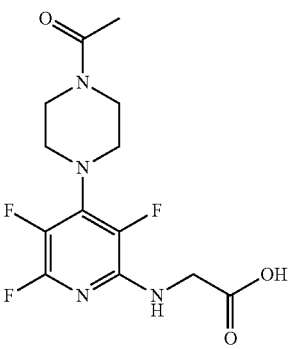 [SMILES: CC(=O)N1CCN(c2c(F)c(F)nc(NCC(=O)O)c2F)CC1]

LiOH (1 M aqueous, 1.49 mL, 1.490 mmol) was added to a solution of ethyl 2-[[4-(4-acetylpiperazin-1-yl)-3,5,6-trifluoropyridin-2-yl]amino]acetate (intermediate 4B) (269 mg, 0.750 mmol) in THF (5 mL) at rt and stirred for 17 h. The reaction mixture was acidified with aqueous HCl (1 M) to ca. pH 6-7 and extracted with EtOAc (3×15 mL), then acidified with aqueous HCl (1 M) to ca. pH 4-5 and extracted with EtOAc (3×15 mL). The combined organic extracts were washed with water and brine (15 mL each), dried (Na$_2$SO$_4$), and the solvent removed under reduced pressure. The residue was triturated with heptane (3×), and dried under reduced pressure to afford a white solid (189 mg, 76%). $^1$H NMR (400 MHz, DMSO-d$_6$): δ 12.48 (br s, 1H), 7.00 (t, J=6.2 Hz, 1H), 3.85 (d, J=6.1 Hz, 2H), 3.58-3.50 (m, 4H), 3.28-3.22 (m, 2H), 2.03 (s, 3H). LRMS (APCI+) m/z 333.1 [M+H]$^+$.

The following intermediate compounds were prepared by the same general procedure.

TABLE 9

Intermediate compounds prepared by the same procedure as compound 13A

| Prep Ex | R | Name | $^1$H NMR δ (400 MHz, DMSO-$d_6$) | LRMS APCI+ |
|---|---|---|---|---|
| 13B | (structure: ethyl 2-{[4-(diethylamino)-3,5,6-trifluoropyridin-2-yl]amino}acetate) | Ethyl 2-{[4-(diethylamino)-3,5,6-trifluoropyridin-2-yl]amino}acetate | 12.48 (s, 1H), 6.87 (t, J = 6.0 Hz, 1H), 3.84 (d, J = 6.2 Hz, 2H), 3.29 (q, J = 7.0 Hz, 4H), 1.09 (t, J = 7.0 Hz, 6H) | 277.9 [M + H]$^+$ |
| 13C | (structure: 2-{[4-(4,4-difluoropiperidin-1-yl)-3,5,6-trifluoropyridin-2-yl]amino}acetic acid) | 2-{[4-(4,4-Difluoropiperidin-1-yl)-3,5,6-trifluoropyridin-2-yl]amino}acetic acid | 12.40 (s, 1H), 7.00 (t, J = 6.3 Hz, 1H), 3.84 (d, J = 6.1 Hz, 2H), 3.41 (t, J = 5.7 Hz, 4H), 2.08 (tt, J = 14.1, 5.7 Hz, 4H) | 325.9 [M + H]$^+$ |

14A: (2S)—N-[(3S)-1-[(4-methoxyl)phenyl)methyl]-2-oxo-5-phenyl-2,3-dihydro-1H-1,4-benzodiazepin-3-yl]-1-(2,3,5,6-tetrafluoropyridin-4-yl)pyrrolidine-2-carboxamide

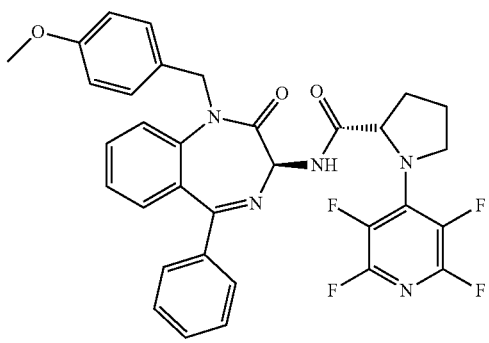

(3S)-3-Amino-1-[(4-methoxyphenyl)methyl]-5-phenyl-3H-1,4-benzodiazepin-2-one (60 mg, 0.16 mmol) was produced according to the procedure described in WO2005/090319. (3S)-3-Amino-1-[(4-methoxyphenyl)methyl]-5-phenyl-3H-1,4-benzodiazepin-2-one (60 mg, 0.16 mmol) and (2S)-1-(2,3,5,6-tetrafluoropyridin-4-yl)pyrrolidine-2-carboxylic acid (intermediate 9E) (64 mg, 0.24 mmol) were dissolved in DMF (1 mL). Triethylamine (0.07 mL, 0.48 mmol) was added followed by 1-[bis(dimethylamino)methylene]-1H-1,2,3-triazolo[4,5-b]pyridinium 3-oxide hexafluorophosphate (HATU) (123 mg, 0.32 mmol) and the mixture stirred at rt for 17 h. Water (15 mL) was added and the mixture extracted with EtOAc (3×10 mL). The combined organics were washed successively with water (3×10 mL), brine (10 mL) and dried (MgSO$_4$). Flash chromatography on SiO$_2$ (35-60% EtOAc:heptane) provided the desired compound (79 mg, 79%) as a white solid. $^1$H NMR (400 MHz, CDCl$_3$) δ 7.90 (d, J=8.5 Hz, 1H), 7.61-7.56 (m, 1H), 7.54-7.48 (m, 2H), 7.38 (t, J=7.8 Hz, 2H), 7.33-7.29 (m, 2H), 7.22 (d, J=4.1 Hz, 2H), 6.95-6.84 (m, 2H), 6.67-6.55 (m, 2H), 5.65 (d, J=8.4 Hz, 1H), 5.61 (d, J=14.9 Hz, 1H), 4.91-4.80 (m, 1H), 4.67 (d, J=14.9 Hz, 1H), 4.21-4.10 (m, 1H), 3.93-3.81 (m, 1H), 3.68 (s, 3H), 2.48-2.39 (m, 1H), 2.37-2.29 (m, 1H), 2.25-2.14 (m, 1H), 2.09-1.99 (m, 1H); LRMS APCI+618.7 [M+H]$^+$.

The following intermediate compounds were prepared by the same general procedure.

TABLE 10

Intermediate compounds of formula (14)

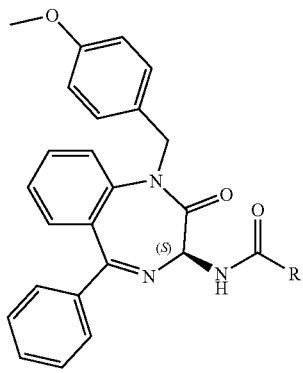

(14)

| Prep Ex | R | Name | $^1$H NMR δ (400 MHz) | LRMS APCI+ | TLC $R_f$ value |
|---|---|---|---|---|---|
| 14B | ![structure with (R)-pyrrolidine linked to tetrafluoropyridine] | (2R)-N-[(3S)-1-[(4-methoxyphenyl)methyl]-2-oxo-5-phenyl-2,3-dihydro-1H-1,4-benzodiazepin-3-yl]-1-(2,3,5,6-tetrafluoropyridin-4-yl)pyrrolidine-2-carboxamide | (CDCl$_3$) δ 8.20 (d, J = 8.2 Hz, 1H), 7.73-7.64 (m, 1H), 7.62-7.55 (m, 2H), 7.45-7.39 (m, 2H), 7.35-7.31 (m, 1H), 7.30-7.20 (m, 2H), 7.02-6.83 (m, 2H), 6.70-6.53 (m, 2H), 5.74 (d, J = 8.2 Hz, 1H), 5.67 (d, J = 14.9 Hz, 1H), 4.97-4.78 (m, 2H), 4.72 (d, J = 14.9 Hz, 1H), 4.22-4.05 (m, 1H), 3.98-3.83 (m, 1H), 3.68 (s, 3H), 2.51-2.42 (m, 2H), 2.27-2.18 (m, 1H), 2.11-2.01 (m, 1H). | 618.7 [M + H]$^+$ | |
| 14C | ![structure with (S)-isobutyl NH linked to tetrafluoropyridine] | (2S)-N-[(3S)-1-[(4-methoxyphenyl)methyl]-2-oxo-5-phenyl-2,3-dihydro-1H-1,4-benzodiazepin-3-yl]-3-methyl-2-[(2,3,5,6-tetrafluoropyridin-4-yl)amino]butanamide | | 619.8 [M + H]$^+$ | 0.55 (EtOAc: heptane; 1:1) |
| 14D | ![structure with (R)-isobutyl NH linked to tetrafluoropyridine] | (2R)-N-[(3S)-1-[(4-methoxyphenyl)methyl]-2-oxo-5-phenyl-2,3-dihydro-1H-1,4-benzodiazepin-3-yl]-3-methyl-2-[(2,3,5,6-tetrafluoropyridin-4-yl)amino]butanamide | | 619.8 [M + H]$^+$ | 0.54 (EtOAc: heptane; 1:1) |
| 14E | ![structure with (S)-methyl NH linked to tetrafluoropyridine] | (2S)-N-[(3S)-1-[(4-methoxyphenyl)methyl]-2-oxo-5-phenyl-3H-1,4-benzodiazepin-3-yl]-2-[(2,3,5,6-tetrafluoropyridin-4-yl)amino]propanamide | (CDCl$_3$) δ 7.96 (d, J = 8.1 Hz, 1H), 7.67-7.49 (m, 3H), 7.45-7.32 (m, 4H), 7.31-7.22 (m, 2H), 6.93 (d, J = 8.7 Hz, 2H), 6.65 (d, J = 8.6 Hz, 2H), 5.81-5.60 (m, 3H), 4.80-4.64 (m, 2H), 3.71 (s, 3H), 1.70 (d, J = 6.9 Hz, 3H). | 591.8 [M + H]$^+$ | 0.68 (CH$_2$Cl$_2$: EtOH: NH$_4$OH; 100:8:1) |

TABLE 10-continued

Intermediate compounds of formula (14)

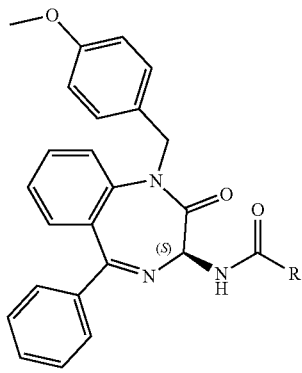

(14)

| Prep Ex | R | Name | ¹H NMR δ (400 MHz) | LRMS APCI+ | TLC R_f value |
|---|---|---|---|---|---|
| 14F | 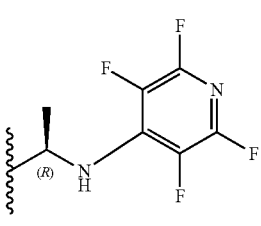 | (2R)-N-[(3S)-1-[(4-methoxyphenyl)methyl]-2-oxo-5-phenyl-3H-1,4-benzodiazepin-3-yl]-2-[(2,3,5,6-tetrafluoropyridin-4-yl)amino]propanamide | (CDCl₃) δ 7.91 (d, J = 8.0 Hz, 1H), 7.56 (ddd, J = 32.2, 7.7, 4.4 Hz, 3H), 7.44-7.20 (m, 7H), 6.94 (d, J = 8.5 Hz, 2H), 6.70-6.56 (m, 2H), 5.77-5.59 (m, 2H), 5.42 (s, 1H), 4.72 (t, J = 12.9 Hz, 2H), 3.71 (s, 3H), 1.74 (d, J = 6.8 Hz, 3H). | 591.6 [M + H]⁺ | 0.72 (CH₂Cl₂: EtOH: NH₄OH; 100:8:1) |
| 14G | 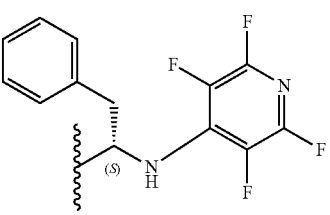 | (2S)-N-[(3S)-1-[(4-methoxyphenyl)methyl]-2-oxo-5-phenyl-2,3-dihydro-1H-1,4-benzodiazepin-3-yl]-3-phenyl-2-[(2,3,5,6-tetrafluoropyridin-4-yl)amino]propanamide | — | 668.9 [M + H]⁺ | 0.48 (EtOAc: heptane; 1:1) |
| 14H | 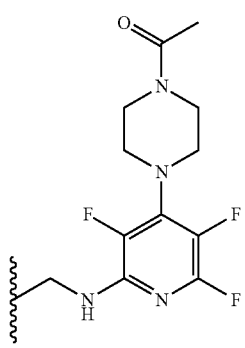 [SMILES: *CNc1nc(F)c(F)c(N2CCN(C(C)=O)CC2)c1F] | 2-[[4-(4-acetylpiperazin-1-yl)-3,5,6-trifluoropyridin-2-yl]amino]-N-[(3S)-1-[(4-methoxyphenyl)methyl]-2-oxo-5-phenyl-3H-1,4-benzodiazepin-3-yl]acetamide | (DMSO-d₆) δ 9.08 (d, J = 8.0 Hz, 1H), 7.78 (dd, J = 8.4, 1.2 Hz, 1H), 7.64 (ddd, J = 8.5, 7.2, 1.6 Hz, 1H), 7.56-7.47 (m, 1H), 7.45-7.36 (m, 2H), 7.32-7.12 (m, 4H), 6.94 (t, J = 6.3 Hz, 2H), 6.89-6.81 (m, 2H), 6.70-6.60 (m, 2H), 5.47 (d, J = 15.2 Hz, 1H), 5.38 (d, J = 8.0 Hz, 1H), 4.87 (d, J = 15.2 Hz, 1H), 4.11-3.92 (m, 2H), 3.64 (s, 3H), 3.61-3.50 (m, 4H), 3.30-3.20 (m, 2H), 2.04 (s, 3H). | 686.3 [M + H]⁺ | 0.39 (CH₂Cl₂: EtOH: NH₄OH; 100:8:1) |

TABLE 10-continued

Intermediate compounds of formula (14)

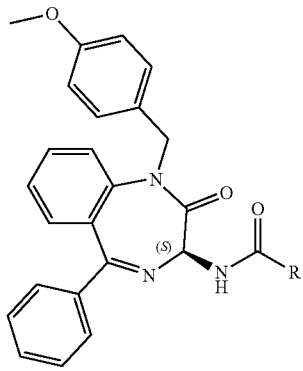

(14)

| Prep Ex | R | Name | $^1$H NMR δ (400 MHz) | LRMS APCI+ | TLC $R_f$ value |
|---|---|---|---|---|---|
| 14J | (thiazinane dioxide-pyridine-F3 group) | 2-[[4-(1,1-dioxo-1,4-thiazinan-4-yl)-3,5,6-trifluoropyridin-2-yl]amino]-N-[(3S)-1-[(4-methoxyphenyl)methyl]-2-oxo-5-phenyl-3H-1,4-benzodiazepin-3-yl]acetamide | (DMSO-d$_6$) δ 9.09 (d, J = 8.0 Hz, 1H), 7.78 (dd, J = 8.4, 1.1 Hz, 1H), 7.65 (ddd, J = 8.5, 7.2, 1.6 Hz, 1H), 7.56-7.47 (m, 1H), 7.45-7.36 (m, 2H), 7.32-7.13 (m, 4H), 7.02 (t, J = 6.0 Hz, 1H), 6.89-6.81 (m, 2H), 6.68-6.60 (m, 2H), 5.47 (d, J = 15.2 Hz, 1H), 5.38 (d, J = 8.0 Hz, 1H), 4.87 (d, J = 15.2 Hz, 1H), 4.12-3.94 (m, 2H), 3.71 (br s, 4H), 3.27 (br s, 4H). | 693.2 [M + H]$^+$ | 0.42 (CH$_2$Cl$_2$: EtOH: NH$_4$OH; 100:8:1) |
| 14K | (morpholino-pyridine-F3 group) | N-[(3S)-1-[(4-ethoxyphenyl)methyl]-2-oxo-5-phenyl-2,3-dihydro-1H-1,4-benzodiazepin-3-yl]-2-{[3,5,6-trifluoro-4-(morpholin-4-yl)pyridin-2-yl]amino} acetamide | (DMSO-d$_6$) δ 9.08 (d, J = 8.1 Hz, 1H), 7.78 (dd, J = 8.4, 1.1 Hz, 1H), 7.65 (ddd, J = 8.4, 7.3, 1.6 Hz, 1H), 7.54-7.48 (m, 1H), 7.45-7.36 (m, 2H), 7.33-7.16 (m, 4H), 6.92 (t, J = 6.1 Hz, 1H), 6.85 (d, J = 8.7 Hz, 2H), 6.64 (d, J = 8.7 Hz, 2H), 5.46 (d, J = 15.2 Hz, 1H), 5.37 (d, J = 8.0 Hz, 1H), 4.87 (d, J = 15.2 Hz, 1H), 4.01 (t, J = 6.4 Hz, 2H), 3.75-3.66 (m, 4H), 3.64 (s, 3H), 3.34-3.29 (m, 4H). | 645.7 [M + H]$^+$ | |

TABLE 10-continued

Intermediate compounds of formula (14)

(14)

| Prep Ex | R | Name | ¹H NMR δ (400 MHz) | LRMS APCI+ | TLC R_f value |
|---|---|---|---|---|---|
| 14L | | 2-{[4-(Diethylamino)-3,5,6-trifluoropyridin-2-yl]amino}-N-[(3S)-1-[(4-methoxyphenyl)methyl]-2-oxo-5-phenyl-2,3-dihydro-1H-1,4-benzodiazepin-3-yl]acetamide | (DMSO-d₆) δ 9.08 (d, J = 8.0 Hz, 1H), 7.77 (dd, J = 8.4, 1.1 Hz, 1H), 7.64 (ddd, J = 8.5, 7.2, 1.6 Hz, 1H), 7.56-7.47 (m, 1H), 7.45-7.35 (m, 2H), 7.31-7.11 (m, 4H), 6.89-6.78 (m, 3H), 6.70-6.56 (m, 2H), 5.46 (d, J = 15.2 Hz, 1H), 5.36 (d, J = 8.1 Hz, 1H), 4.86 (d, J = 15.2 Hz, 1H), 4.08-3.94 (m, 2H), 3.63 (s, 3H), 3.29 (q, J = 7.1 Hz, 4H), 1.09 (t, J = 7.0 Hz, 6H). | 631.3 [M + H]⁺ | |
| 14M | | N-[(3S)-1-[(4-Methoxyphenyl)methyl]-2-oxo-5-phenyl-2,3-dihydro-1H-1,4-benzodiazepin-3-yl]-2-[(2,3,5-trifluoro-6-methanesulfonylpyridin-4-yl)amino]acetamide | | 638.5 [M + H]⁺ | 0.81 (EtOAc) |

Procedure for Deprotection

Compounds: (2S)—N-[(3S)-2-oxo-5-phenyl-2,3-dihydro-1H-1,4-benzodiazepin-3-yl]-1-(2,3,5,6-tetrafluoropyridin-4-yl)pyrrolidine-2-carboxamide

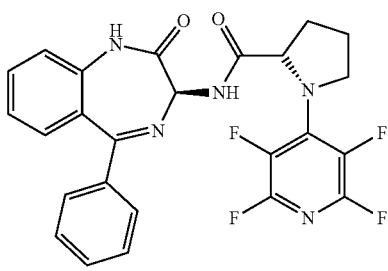

AlCl₃ (201 mg, 1.48 mmol) was added to a solution of (2S)—N-[(3S)-1-[(4-methoxyphenyl)methyl]-2-oxo-5-phenyl-3H-1,4-benzodiazepin-3-yl]-1-(2,3,5,6-tetrafluoropyridin-4-yl)pyrrolidine-2-carboxamide (intermediate 14C) (76 mg, 0.12 mmol) in anhydrous anisole (1.5 mL) and the mixture stirred at rt for 40 h. The mixture was cooled to 0° C., quenched with water (10 mL), and extracted with CH₂Cl₂ (4×10 mL). The organics were washed with brine (15 mL) and dried (Na₂SO₄). Flash chromatography on SiO₂ (30-45% EtOAc:heptane) provided the desired compound as a white solid (24 mg, 39%). ¹H NMR (400 MHz, CDCl₃) δ 8.59 (s, 1H), 7.67-7.47 (m, 2H), 7.45-7.34 (m, 3H), 7.26-7.18 (m, 2H), 5.55 (d, J=8.4 Hz, 1H), 4.91-4.79 (m, 1H), 4.13-4.05 (m, 1H), 3.94-3.78 (m, 1H), 2.39 (dt, J=14.9, 7.5 Hz, 1H), 2.24 (dd, J=13.1, 6.4 Hz, 1H), 2.13 (dt, J=13.1, 6.4 Hz, 1H), 2.03-1.95 (m, 1H). LRMS APCI+498.8 [M+H]⁺.

The following compounds were prepared by the same general procedure.

TABLE 11

Benzodiazepines compounds of formula (VI)

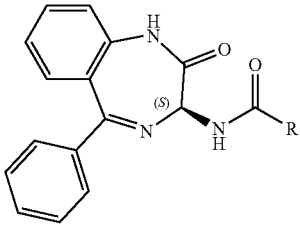

(VI)

| Cmpd | R | Name | $^1$H NMR δ (400 MHz) | LRMS APCI+ |
|---|---|---|---|---|
| 6 | (R)-pyrrolidinyl-tetrafluoropyridine | N(2R)-N-[(3S)-2-oxo-5-phenyl-2,3-dihydro-1H-1,4-benzomazepin-3-yl]-1-(2,3,5,6-tetrafluoropyridin-4-yl)pyrrolidine-2-carboxamide | (CDCl$_3$) δ 7.72-7.54 (m, 4H), 7.53-7.36 (m, 4H), 7.34 (dd, J = 8.0, 1.6 Hz, 1H), 7.29-7.23 (m, 1H), 5.53 (d, J = 7.9 Hz, 1H), 4.69 (s, 1H), 4.03 (s, 1H), 3.89-3.79 (m, 1H), 2.28 (d, J = 6.8 Hz, 2H), 2.19-2.06 (m, 2H), 2.02-1.89 (m, 2H). | 498.8 [M + H]$^+$ |
| 7 | (S)-isopropyl-NH-tetrafluoropyridine | (2S)-3-Methyl-N-[(3S)-2-oxo-5-phenyl-2,3-dihydro-1H-1,4-benzodiazepin-3-yl]-2-[(2,3,5,6-tetrafluoropyridin-4-yl)amino]butanamide | (DMSO-d$_6$) δ 7.73-7.27 (m, 9H), 5.62 (d, J = 8.0 Hz, 1H), 5.43 (br s, 1H), 4.44 (br s, 1H), 2.24 (br s, 1H), 1.18-1.00 (m, 6H) | 499.8 [M + H]$^+$ |
| 8 | (R)-isopropyl-NH-tetrafluoropyridine | (2R)-3-Methyl-N-[(3S)-2-oxo-5-phenyl-2,3-dihydro-1H-1,4-benzodiazepin-3-yl]-2-[(2,3,5,6-tetrafluoropyridin-4-yl)amino]butanamide | (DMSO-d$_6$) δ 7.81-7.30 (m, 9H), 5.58 (d, J = 8.2 Hz, 1H), 5.06-5.01 (m, 1H), 4.18 (br s, 1H), 2.22 (br s, 1H), 1.13-0.99 (m, 6H) | 499.8 [M + H]$^+$ |
| 9 | (S)-methyl-NH-tetrafluoropyridine | (2S)-N-[(3S)-2-oxo-5-phenyl-1,3-dihydro-1,4-benzodiazepin-3-yl]-2-[(2,3,5,6-tetrafluoropyridin-4-yl)amino]propanamide | (CDCl$_3$) δ 7.76-7.18 (m, 11H), 5.57 (d, J = 7.9 Hz, 2H), 4.65 (t, J = 7.1 Hz, 1H), 1.61 (d, J = 6.8 Hz, 3H) | 471.8 [M + H]$^+$ |
| 10 | (R)-methyl-NH-tetrafluoropyridine | (2R)-N-[(3S)-2-oxo-5-phenyl-1,3-dihydro-1,4-benzodiazepin-3-yl]-2-[(2,3,5,6-tetrafluoropyridin-4-yl)amino]propanamide | (CDCl$_3$) δ 7.65-7.29 (m, 11H), 5.57 (d, J = 7.8 Hz, 1H), 5.38 (d, J = 7.5 Hz, 1H), 4.60 (s, 1H), 1.66 (d, J = 6.9 Hz, 3H) | 471.7 [M + H]$^+$ |

TABLE 11-continued

Benzodiazepines compounds of formula (VI)

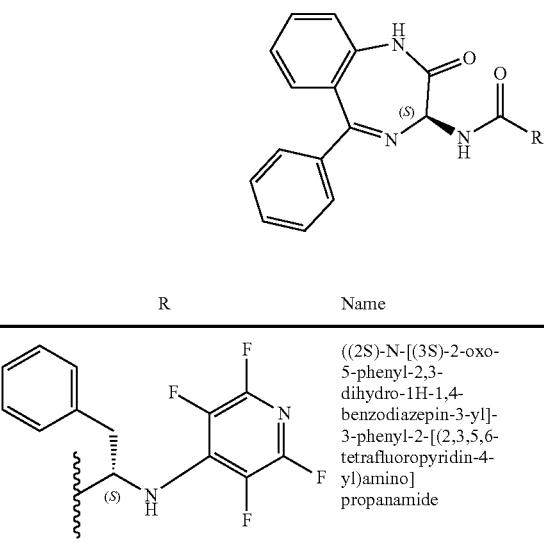

| Cmpd | R | Name | $^1$H NMR δ (400 MHz) | LRMS APCI+ |
|---|---|---|---|---|
| 11 | | ((2S)-N-[(3S)-2-oxo-5-phenyl-2,3-dihydro-1H-1,4-benzodiazepin-3-yl]-3-phenyl-2-[(2,3,5,6-tetrafluoropyridin-4-yl)amino] propanamide | (DMSO-d$_6$) δ 10.93 (s, 1H), 9.64 (d, J = 7.9 Hz, 1H), 7.65 (ddd, J = 8.5, 7.2, 1.7 Hz, 1H), 7.58-7.42 (m, 6H), 7.37-7.23 (m, 5H), 7.19 (t, J = 7.4 Hz, 1H), 7.02 (d, J = 9.4 Hz, 1H), 5.26 (d, J = 7.8 Hz, 1H), 4.92 (t, J = 9.7 Hz, 1H), 3.21-3.06 (m, 1H) | 548.2 [M + H]$^+$ |
| 12 | | 2-[[4-(4-acetylpiperazin-1-yl)-3,5,6-trifluoropyridin-2-yl]amino]-N-[(3S)-2-oxo-5-phenyl-1,3-dihydro-1,4-benzodiazepin-3-yl]acetamide | (DMSO-d6) δ 10.90 (s, 1H), 9.02 (d, J = 8.1 Hz, 1H), 7.64 (ddd, J = 8.7, 7.1, 1.7 Hz, 1H), 7.57-7.40 (m, 5H), 7.37-7.18 (m, 3H), 6.93 (td, J = 6.3, 3.1 Hz, 1H), 5.24 (d, J = 8.0 Hz, 1H), 4.13-3.92 (m, 2H), 3.62-3.48 (m, 4H), 3.26 (d, J = 5.5 Hz, 2H), 2.04 (s, 3H) | 566.2 [M + H]$^+$ |
| 13 | | 2-[[4-(1,1-dioxo-1,4-thiazinan-4-yl)-3,5,6-trifluoropyridin-2-yl]amino]-N-[(3S)-2-oxo-5-phenyl-1,3-dihydro-1,4-benzodiazepin-3-yl]acetamide | (DMSO-d6) δ 10.92 (s, 1H), 9.03 (d, J = 8.1 Hz, 1H), 7.64 (ddd, J = 8.6, 7.1, 1.7 Hz, 1H), 7.56-7.39 (m, 5H), 7.35-7.21 (m, 3H), 7.06-6.98 (m, 1H), 5.24 (d, J = 8.0 Hz, 1H), 4.10-3.93 (m, 2H), 3.72 (br s, 4H), 3.32-3.21 (m, 4H) | 573.2 [M + H]$^+$ |
| 14 | | N-[(3S)-2-oxo-5-phenyl-2,3-dihydro-1H-1,4-benzodiazepin-3-yl]-2-{[3,5,6-trifluoro-4-(morpholin-4-yl)pyridin-2-yl]amino}acetamide yl]amino}acetamide | (DMSO-d$_6$) δ 10.91 (s, 1H), 9.02 (d, J = 8.1 Hz, 1H), 7.64 (ddd, J = 8.7, 7.1, 1.7 Hz, 1H), 7.56-7.42 (m, 5H), 7.38-7.21 (m, 3H), 6.92 (t, J = 6.4 Hz, 1H), 5.23 (d, J = 8.1 Hz, 1H), 4.14-3.95 (m, 2H), 3.69 (dd, J = 5.6, 3.7 Hz, 4H), 3.32 (d, J = 5.6, 3.7 Hz, 4H) | 525.0 [M + H]$^+$ |

TABLE 11-continued

Benzodiazepines compounds of formula (VI)

(VI)

| Cmpd | R | Name | $^1$H NMR δ (400 MHz) | LRMS APCI+ |
|---|---|---|---|---|
| 15 | (diethylamino pyridyl structure) | 2-{[4-(diethylamino)-3,5,6-trifluoropyridin-2-yl]amino}-N-[(3S)-2-oxo-5-phenyl-2,3-dihydro-1H-1,4-benzodiazepin-3-yl]acetamide | (DMSO-d$_6$) δ 10.90 (s, 1H), 8.99 (d, J = 8.0 Hz, 1H), 7.63 (ddd, J = 8.7, 7.1, 1.7 Hz, 1H), 7.56-7.42 (m, 5H), 7.33-7.21 (m, 3H), 6.80 (t, J = 6.3 Hz, 1H), 5.23 (d, J = 8.0 Hz, 1H), 4.07-3.92 (m, 2H), 3.32-3.23 (m, 4H), 1.09 (t, J = 7.0 Hz, 6H) | 511.2 [M + H]$^+$ |
| 16 | (methanesulfonyl pyridyl structure) | N-[(3S)-2-oxo-5-phenyl-2,3-dihydro-1H-1,4-benzodiazepin-3-yl]-2-[(2,3,5-trifluoro-6-methanesulfonylpyridin-4-yl)amino]acetamide | (CDCl$_3$) δ 12.02 (s, 1H), 7.91-7.75 (m, 4H), 7.75-7.57 (m, 4H), 7.43-7.35 (m, 2H), 6.05 (s, 1H), 5.52 (s, 1H), 4.25 (s, 1H), 4.17-4.08 (m, J = 1H), 3.24 (s, 3H) | APCI+ 518.0 [M + H]$^+$ |

Compound 17: 2-{[4-(4,4-Difluoropiperidin-1-yl-6-trifluoropridin-2-yl]amino}-N-[(3S)-2-oxo-1-phenyl-2-dihydro-1H-1,4-benzodiazepin-3-yl]acetamide

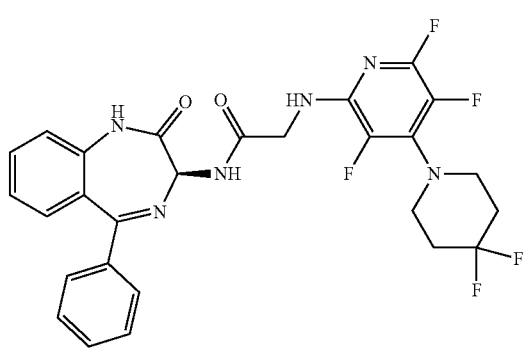 [SMILES: O=C(CNc1nc(F)c(F)c(N2CCC(F)(F)CC2)c1F)N[C@H]1N=C(c2ccccc2)c2ccccc2NC1=O]

(3S)-3-Amino-5-phenyl-1,3-dihydro-1,4-benzodiazepin-2-one (90 mg, 0.36 mmol) and 2-[[4-(4,4-difluoropiperidin-1-yl)-3,5,6-trifluoropyridin-2-yl]amino]acetic acid (intermediate 13C) (128 mg, 0.39 mmol, 1.1 eq.) were dissolved in DMF (2 mL). Triethylamine (0.10 mL, 0.72 mmol, 2 eq.) was added followed by HATU (150 mg, 0.39 mmol) The mixture was stirred at rt for 17 h. Water (20 mL) was added, the mixture was extracted with EtOAc (3×15 mL). The organics were washed with water (is mL) and brine (15 mL) and dried (MgSO$_4$). Flash chromatography on SiO$_2$ (50-80% EtOAc:heptane) provided the desired compound as a white solid (144 mg, 72%). $^1$H NMR (400 MHz, DMSO-d$_6$) δ 10.90 (s, 1H), 9.01 (d, J=8.1 Hz, 1H), 7.64 (ddd, J=8.6, 7-1, 1.7 Hz, 1H), 7.59-7.39 (m, 4H), 7.36-7.23 (m, 3H), 6.94 (t, J=6.4 Hz, 1H), 5.24 (d, J=8.1 Hz, 1H), 4.08-3.93 (m, 2H), 3.50-3.38 (m, 4H), 2.18-2.04 (m, 4H). LRMS APCI+559.2 [M+H]$^+$.

Compound 18: 2-[(6-Chloropyrimidin-4-yl)amino]-N-[(3S)-2-oxo-5-phenyl-2,3-dihydro-1H-1,4-benzodiazepin-3-yl]acetamide Tert-butyl-2{(6-chloropyrimidin-4-yl)amino]acetate

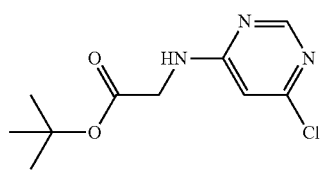 [SMILES: CC(C)(C)OC(=O)CNc1cc(Cl)ncn1]

4,6-Dichloropyrimidine (4.00 g, 26.9 mmol) and glycine tert butyl ester hydrochloride (5.50 g, 26.9 mmol) were dissolved in EtOH (30 mL). Diisopropylethylamine (9.35 mL, 53.7 mmol) was added and the resulting solution was heated at 70° C. for 18 h. The mixture was allowed to cool to rt and solvent was removed under reduced pressure. The mixture was diluted with EtOAc (50 mL), washed with water (2×5 mL), brine (50 mL) and dried (MgSO$_4$). Flash chromatography on SiO$_2$ [20-50% (50:8:1 CH$_2$Cl$_2$:EtOH: NH$_4$OH in CH$_2$Cl$_2$)] provided the desired compound as a white solid (4.85 g, 74%). $^1$H NMR (400 MHz, CDCl$_3$) δ 8.38 (d, J=0.9 Hz, 1H), 6.41 (s, 1H), 5.53 (s, 1H), 4.04 (s, 2H), 1.49 (s, 9H). LRMS APCI+243.8 [M+H]$^+$.

2{(6-Chloropyrimidin-4-yl)amino]acetic acid hydrochloride

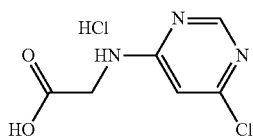 [SMILES: O=C(O)CNc1cc(Cl)ncn1 ; Cl]

HCl (2M in Et$_2$O, 2 mL, 4.00 mmol) was added to tert-butyl 2-[(6-chloropyrimidin-4-yl)amino]acetate (100 mg, 0.41 mmol) followed by 1,4-dioxane (5 mL). Water (3 mL) was added to give a solution. The mixture was stirred at rt for 48 h. The mixture was concentrated under reduced pressure providing the desired compound crude (110 mg, 120%) as a white solid. LRMS APCI+541.9 [M+H]$^+$. R$_f$=0.01 (EtOAc).

2{(6-Chloropyrimidin-4-yl)amino]-N{(3S)-1{(4-methoxyphenyl)methyl-2-oxo-5-phenyl-2,3-dihydro-1H-1,4-benzodiazepin-3-yl]acetamide

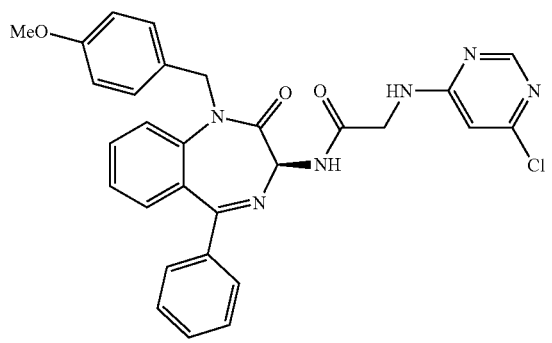 [SMILES: COc1ccc(CN2C(=O)[C@@H](NC(=O)CNc3cc(Cl)ncn3)N=C(c3ccccc3)c3ccccc32)cc1]

Prepared by an analogous procedure to that described for intermediate 14A from 2-[(6-chloropyrimidin-4-yl)amino] acetic acid hydrochloride. LRMS APCI+541.9 [M+H]$^+$. R$_f$=0.35 (200:8:1 CH$_2$Cl$_2$:EtOH:NH$_4$OH).

2{(6-Chloropyrimidin-4-yl)amino]-N{(3S)-2-oxo-5-phenyl-2,3-dihydro-1H-1,4-benzodiazepin-3-yl]acetamide

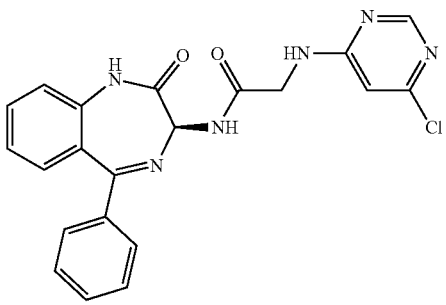 [SMILES: O=C(CNc1cc(Cl)ncn1)N[C@H]1N=C(c2ccccc2)c2ccccc2NC1=O]

Prepared by an analogous procedure to that described for compound 5 from 2-[(6-chloropyrimidin-4-yl)amino]-N-[(3S)-1-[(4-methoxyphenyl)methyl]-2-oxo-5-phenyl-3H-1,4-benzodiazepin-3-yl]acetamide. $^1$H NMR (400 MHz, CDCl$_3$) δ 10.90 (s, 1H), 9.24 (d, J=7.8 Hz, 1H), 8.29 (s, 1H), 7.96 (t, J=5.9 Hz, 1H), 7.64 (ddd, J=8.6, 7.2, 1.7 Hz, 1H), 7.58-7.35 (m, 5H), 7.35-7.15 (m, 3H), 6.69 (s, 1H), 5.24 (d, J=8.0 Hz, 1H), 4.25-4.08 (m, 2H). LRMS APCI+422.7 [M+H]$^+$.

Compound 19: 2-{[6-(4 Methanesulfonylpiperazin-1-yl)pyrimidin-4-yl]amino-N-[(3S)-2-oxo-5-phenyl-2,3-dihydro-1H-1,4-benzodiazepin-3-yl]acetamide

Tert-butyl 2-{[6-(4-methanesulfonylpiperazin-1-yl)pyrimidin-4-yl]amino}acetate

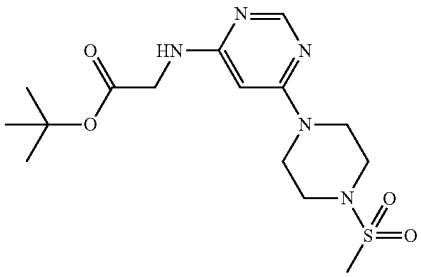 [SMILES: CC(C)(C)OC(=O)CNc1cc(N2CCN(S(C)(=O)=O)CC2)ncn1]

A solution of 1-(methylsulfonyl)piperazine (172.4 mg, 1.05 mmol) and tert-butyl 2-[(6-chloropyrimidin-4-yl) amino]acetate (122 mg, 0.50 mmol) in 1-butanol (2 mL) was heated in an ACE pressure tube at 150° C. for 22 h. The mixture was cooled to rt and the solvent removed under reduced pressure. Flash chromatography on SiO$_2$ [10-25% (50:8:1 CH$_2$Cl$_2$:EtOH:NH$_4$OH in CH$_2$Cl$_2$)] provided the desired compound as an off-white solid (123 mg, 66%). $^1$H NMR (400 MHz, CDCl$_3$) δ 8.20 (d, J=0.9 Hz, 1H), 5.48 (s, 1H), 5.12 (s, 1H), 3.99 (d, J=5.3 Hz, 2H), 3.76-3.64 (m, 4H), 3.33-3.18 (m, 4H), 2.79 (s, 3H), 1.48 (s, 7H). LRMS APCI+371.7 [M+H]⁺.

2-{[6-(4-Methanesulfonylpiperazin-1-yl)pyrimidin-4-yl]amino}acetic acid hydrochloride

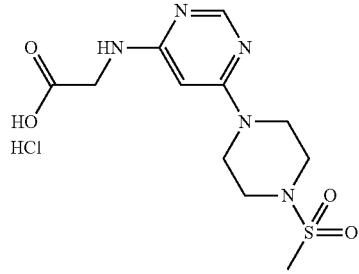 [SMILES: Cl ; CS(=O)(=O)N1CCN(c2cc(NCC(=O)O)ncn2)CC1]

HCl (2 M in Et2O; 3.38 mL, 6.76 mmol) was added to tert-butyl 2-[[6-(4-methylsulfonylpiperazin-1-yl)pyrimidin-4-yl]amino]acetate (126 mg, 0.34 mmol) and the mixture was stirred at rt for 48 h. Water (3 mL) was added to give a solution and the mixture was stirred for a further 18 h. The mixture was concentrated and used directly without purification. LRMS APCI+371.7 [M+H]⁺. $R_f$=0.01 (EtOAc)

2-{[6-(4-Methanesulfonylpiperazin-1-yl)pyrimidin-4-yl]amino}-N{(3S)-1{(4-methoxyphenyl)methyl]-2-oxo-5-phenyl-2,3-dihydro-1H-1,4-benzodiazepin-3-yl]acetamide

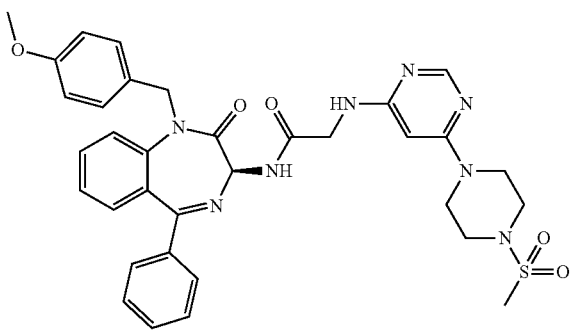 [SMILES: COc1ccc(CN2C(=O)[C@@H](NC(=O)CNc3cc(N4CCN(S(C)(=O)=O)CC4)ncn3)N=C(c3ccccc3)c3ccccc32)cc1]

Prepared by an analogous procedure to that described for intermediate 14A from 2-[[6-(4-methylsulfonylpiperazin-1-yl)pyrimidin-4-yl]amino]acetic acid hydrochloride. ¹H NMR (400 MHz, CDCl₃) δ 8.19 (d, J=0.8 Hz, 1H), 7.96 (d, J=7.6 Hz, 1H), 7.49 (dd, J=6.5, 2.1 Hz, 1H), 7.47-7.41 (m, 2H), 7.35-7.23 (m, 4H), 7.23-7.12 (m, 3H), 6.91-6.87 (m, 2H), 6.64-6.60 (m, 2H), 6.30 (s, 1H), 5.57 (d, J=7.5 Hz, 1H), 5.51 (d, J=15.1 Hz, 1H), 4.71 (d, J=15.1 Hz, 1H), 4.22-4.00 (m, 2H), 3.87-3.67 (m, 4H), 3.67 (s, 3H), 3.35-3.16 (m, 4H), 2.80 (s, 3H). $R_f$=0.09 (200:8:1CH₂C₂:EtOH:NH₄OH)

2-{[6-(4-Methanesulfonylpiperazin-1-yl)pyrimidin-4-yl]amino}-N{(3S)-2-oxo-5-phenyl-2,3-dihydro-1H-1,4-benzodiazepin-3-yl]acetamide

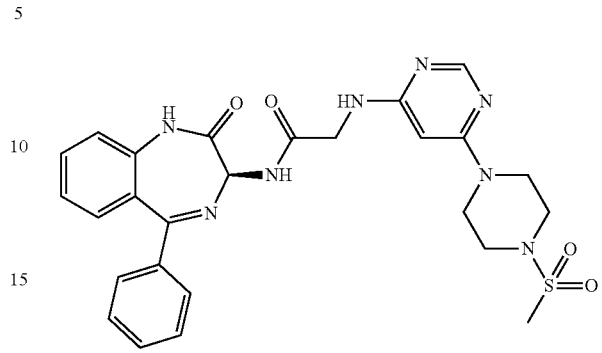

Prepared by an analogous procedure to that described for compound 5 from N-[(3S)-1-[(4-methoxyphenyl)methyl]-2-oxo-5-phenyl-3H-1,4-benzodiazepin-3-yl]-2-[[6-(4-methylsulfonylpiperazin-1-yl)pyrimidin-4-yl]amino]acetamide H NMR (400 MHz, DMSO-d₆) δ 10.91 (s, 1H), 9.14 (d, J=8.0 Hz, 1H), 8.13 (s, 1H), 7.70-7.62 (m, 1H), 7.56-7.50 (m, 1H), 7.50-7.43 (m, 4H), 7.38-7.21 (m, 4H), 5.23 (d, J=7.9 Hz, 1H), 4.29-4.11 (m, 2H), 3.57-3.46 (m, 4H), 3.39-3.31 (m, 1H), 3.26-3.13 (m, 4H), 2.90 (s, 3H). $R_f$=0.03 (200:8:1 CH₂Cl₂:EtOH:NH₄OH).

Example 7: Antiviral and Cell Toxicity Assays

Cells were obtained from ATCC and the virus preparation was subjected to one round of centrifugation through a 40% (V/V) glycerol to remove any interferon produced from infected cells. Growth medium was Dulbecco's modified Eagle's medium (DMEM) with 10% (v/v) foetal calf serum (FCS), Viral maintenance medium was DMEM+2% (v/v) FCS.

Second Plaque Reduction Assay

The RSV plaque reduction assay is an infectivity assay which allows quantification of the number of infectious units in a distinct foci of RSV infection. This is indicated by zones of viral antigen detected by specific antibody staining within a monolayer of otherwise healthy tissue culture cells. As each plaque originates from a single infectious virus particle an accurate calculation of the anti-viral effect can be obtained by counting plaques in the presence and absence of an anti-viral compound. HEp-2 cells (ATCC, CCL23) were passaged in flasks and seeded in 96-well plates in DMEM containing antibiotics and supplemented with 10% FBS. During inoculation and subsequent incubation, cells were cultured in DMEM containing 3% FBS. 100 plaque forming unit (PFU)/well of RSV (RSV A2 VR-1540) was mixed with ten serial dilutions of compound. Subsequently, 100 μL of the virus/compound mixtures was added to confluent HEp-2 cell monolayers. The cells and virus/compound mixtures were incubated at 35° C. in a humidified 5% CO2 incubator for 1 day.

Cells were washed twice with PBS before adding 50% v/v EtOH/MeOH, and then stored at −20° C. On the day of the staining, fixative was first removed from the plates. Plates were washed 3× with PBS. A pre-titrated amount of the primary antibody was added in 60 μL PBS/2% milk powder, and plates incubated for 1 h at rt. The plates were washed 3× with PBS/0.05% Tween20 before addition of goat antimouse horse radish peroxidase in 60 μL PBS/2% milk powder, and incubated for 1 h at rt. Following three wash steps with PBS/0.05% Tween20, 60 μL ready-to-use True-Blue was added and plates were incubated at rt for 10-15 min before adding MilliQ water. Plates were washed once with water, incubated for 30-60 min and after removal of water, air-dried in the dark.

Plates were scanned and analyzed using the Immunospot S6 UV analyzer, which is equipped with BioSpot analysis software for counting immunostained plaques (virospots). Plaque counts were used to calculate % infection relative to the mean of the spot count (SC) in the virus control wells for RSV. IC50/IC90 values were calculated as 50% or 90% reduction in signal, respectively, by interpolation of inhibition curves fitted with a 4-parameter nonlinear regression with a variable slope in GraphPad 5.0 (Prism).

Cell Cytotoxicity—CC50 (Concentration at which 50% Cell Toxicity is Observed):

HepG2 cells, in media supplemented with 10% fetal bovine serum (FBS), were seeded at $4 \times 10^5$ cells/well into white walled 96 well plates and incubated at 37° C., 5% $CO_2$. Twenty-four hours post seeding media was removed and replaced with media supplemented with 2% FBS and containing final compound concentrations equal to those tested in parallel virus plaque assays. Following a further 48-hour incubation cell cytotoxicity was determined using the CellTox™ Green (Promega) kit and luminescence read using an appropriate protocol on a GloMax® Explorer System (Promega). During analysis DMSO containing wells were used as a negative control and lysed cells as a positive control.

TABLE 12

| Compound | Results of second plaque reduction assay and cell cytotoxicity assay | | |
|---|---|---|---|
| | Plaque $IC_{50}$ | Tox $CC_{50}$ | Stereochem |
| 9 | 5.22, 3.76 | >25 | SS |
| 10 | 3.38, 1.79 | >25 | SR |
| 7 | 5.18, 8.68, 10 | 16, >25 | SS |
| 8 | 4.73, 8.33, 9.5 | >25, 16.3 | SR |
| 11 | 1.69, 5.02 | >25, >25 | SS |
| 6 | 4.39, 8.33 | >25 | SR |
| 14 | 0.336, 1.26 | >25 | S |
| 18 | 4.93, 9.33 | >25 | S |

Multiple values are given in Table 12 where multiple test occasions were carried out.

Results and Discussion

The results show that the above tested compounds may be used to treat RSV.

Furthermore, the compounds are effective at non-toxic concentrations.

CONCLUSION

Compounds described herein have been shown to be inhibitors of RSV. Furthermore, the compounds are effective at non-toxic concentrations. One of these compounds (compound 2) is orally bioavailable in mice.

The invention claimed is:
1. A compound of formula (I):

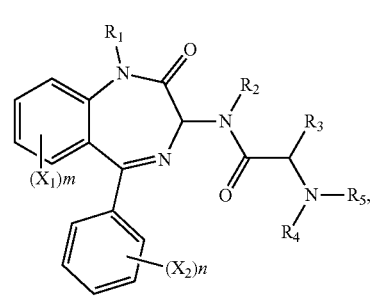

Formula (I)

wherein $R_1$ is H;
$R_2$ is H;
$R_3$ is a side chain of a naturally occurring amino acid; and $R_4$ is H; or $R_3$ and $R_4$, together with the atoms to which they are attached, combine to form a five-membered heterocyclic ring;
$R_5$ is an aromatic six membered ring optionally substituted with one or more substituents, wherein the or each substituent is independently a $C_{1-5}$ straight or branched alkyl or alkenyl, a halogen, $SR_6$, $SO_2R_6$, $OR_6$, or $NR_6R_7$;
m is 0, 1, 2, 3 or 4;
n is 0, 1, 2, 3, 4 or 5;
the or each $X_1$ is independently selected from a $C_{1-5}$ straight or branched alkyl or alkenyl, a halogen, $SR_6$, $SO_2R_6$, $OR_6$ or $NR_6R_7$;
the or each X2 is independently selected from a C1-5 straight or branched alkyl or alkenyl, chlorine, bromine, $SR_6$, $SO_2R_6$, $OR_6$ or $NR_6R_7$;
the or each $R_6$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

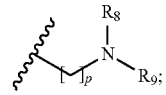

the or each $R_7$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

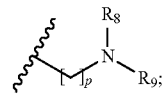

and/or $R_6$ and $R_7$ together with the nitrogen atom to which they are attached independently form a 3-7 membered ring which is optionally substituted with one or more substituents, wherein the or each substituent is independently a $C_{1-5}$ straight or branched alkyl or alkenyl, a halogen, $C(O)R_{10}$, $SR_{10}$, $SO_2R_{10}$, $OR_{10}$ or $NR_{10}R_{11}$;

the or each $R_{10}$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

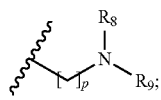

the or each $R_{11}$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

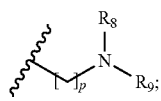

p is 1, 2, 3, 4 or 5; and
$R_8$ and $R_9$ together with the nitrogen atom to which they are attached independently form a 3-7 membered ring; or a pharmaceutically acceptable salt, solvate, tautomeric form or polymorphic form thereof.

2. The compound according to claim 1, wherein m is 0 and n is 0.

3. The compound according to claim 1, wherein $R_3$ is not a cysteine side chain and/or $R_3$ is hydrogen, methyl, isopropyl or benzyl.

4. The compound according to claim 1, wherein $R_5$ is selected from the group consisting of:

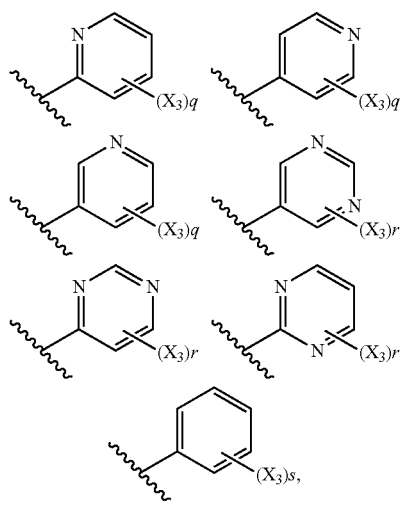

wherein:
q is 0, 1, 2, 3 or 4;
r is 0, 1, 2 or 3;
s is 0, 1, 2, 3, 4 or 5; and
$X_3$ is independently a C1s straight or branched alkyl or alkenyl, a halogen, $SR_6$, $SO_2R_6$, $OR_6$, or $NR_6R_7$.

5. The compound according to claim 4, wherein $R_5$ is selected from the group consisting of:

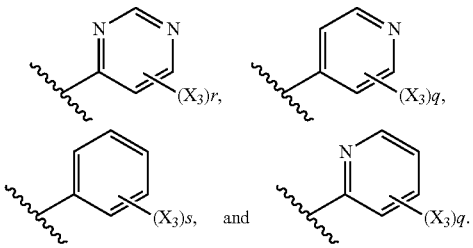

6. The compound according to claim 1, wherein $R_5$ is a phenyl group.

7. The compound according to claim 4, wherein the compound has Formula (Ij):

Formula (Ij)

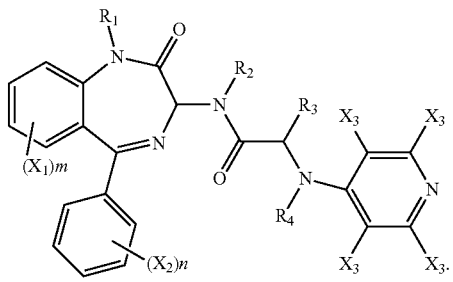

8. The compound according to claim 7, wherein at least one $X_3$ group is a halogen.

9. The compound according to claim 8, wherein three $X_3$ groups are fluorine and one $X_3$ group is selected from fluorine, OEt, $SO_2Me$ and $NR_6R_7$, wherein $R_6$ and $R_7$ are each ethyl or $R_6$ and $R_7$ together with the nitrogen atom to which they are attached independently form a 3-7 membered ring wherein the or each substituent is independently a C1-5 straight or branched alkyl or alkenyl, a halogen, $C(O)R_{10}$, $SR_{10}$, $SO_2R_{10}$, $OR_{10}$ or $NR_{10}R_{11}$.

10. The compound according to claim 4, wherein the compound has Formula (IIh):

Formula (IIh)

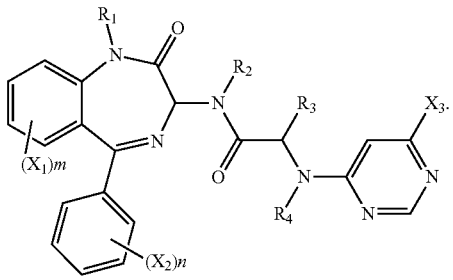

11. The compound according to claim 1, wherein the compound has Formula (Im):

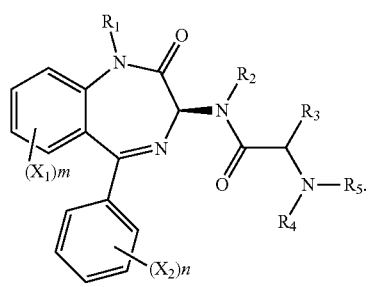
Formula (Im)
12. The compound according to claim 1, selected from the group consisting of:
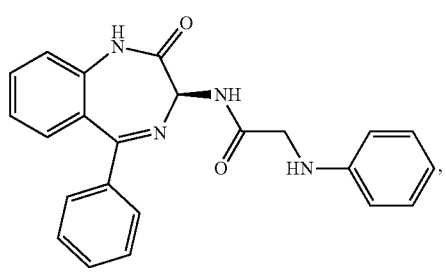
Formula (In)
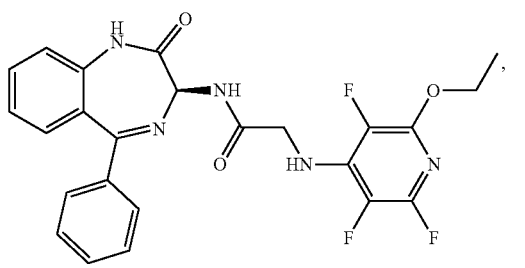
Formula (Io)
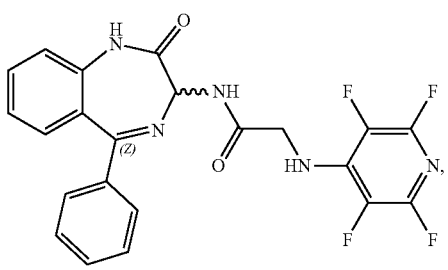
Formula (Ip)
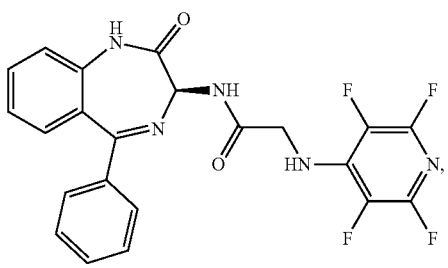
Formula (Iq)
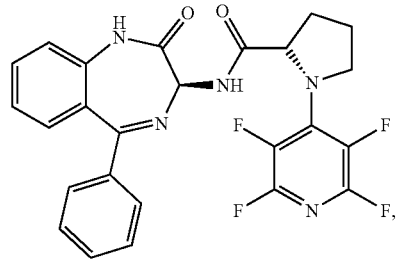
Formula (Ira)
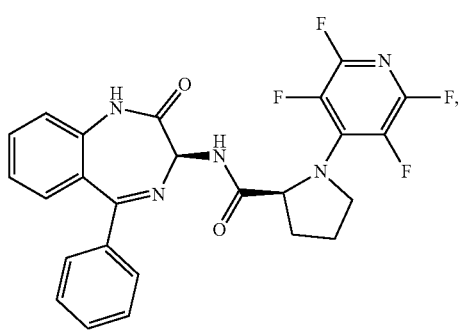
Formula (Irb)
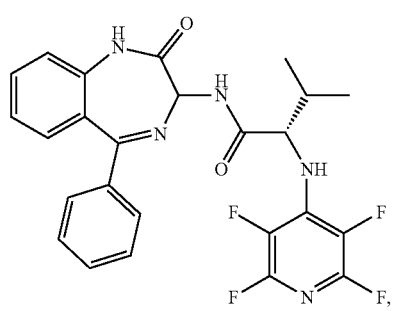
Formula (Irc)
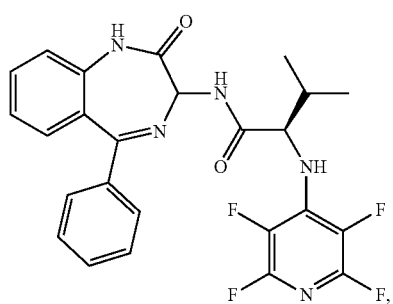
Formula (Ird)
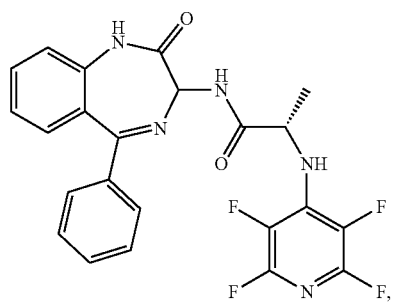
Formula (Ire)

Formula (Irf)
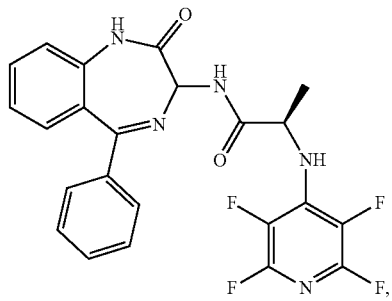
Formula (Irg)
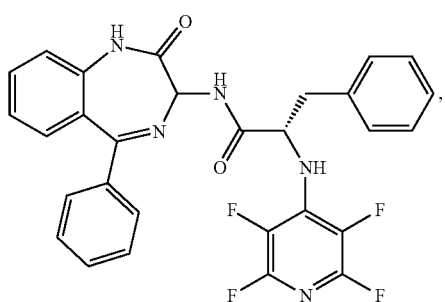
Formula (Irh)
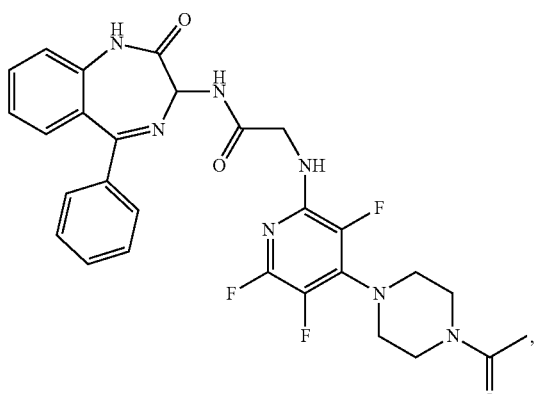
Formula (Iri)
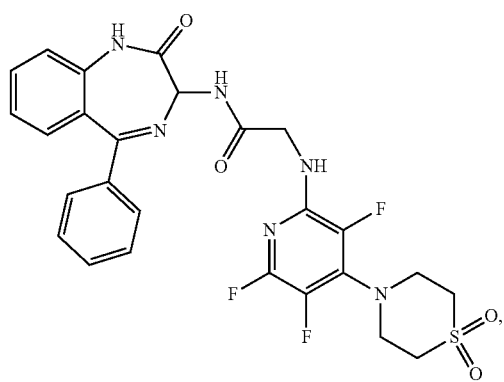
Formula (Irj)
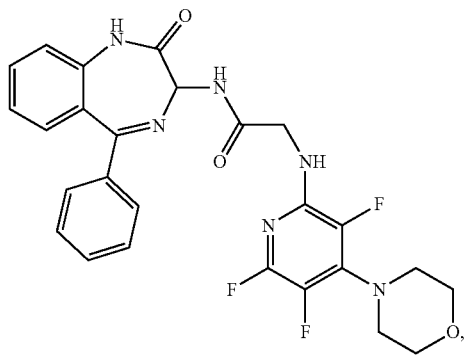
Formula (Irk)
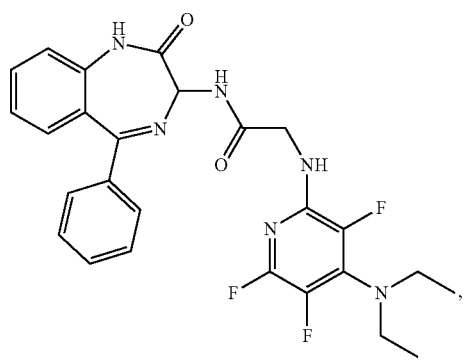
Formula (Irl)
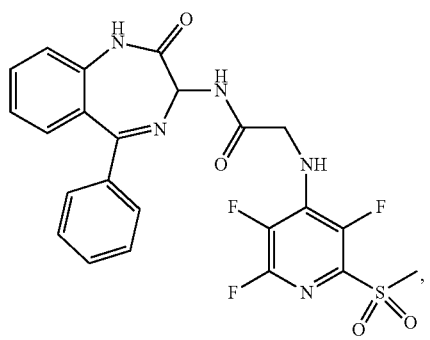
Formula (Irm)
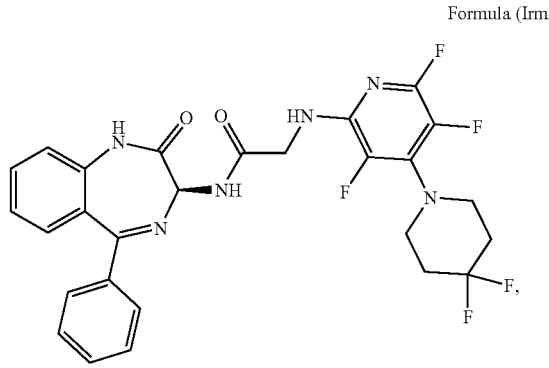

Formula (Irn)

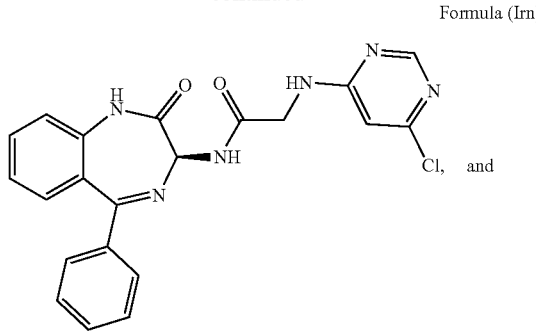

Formula (Iro)

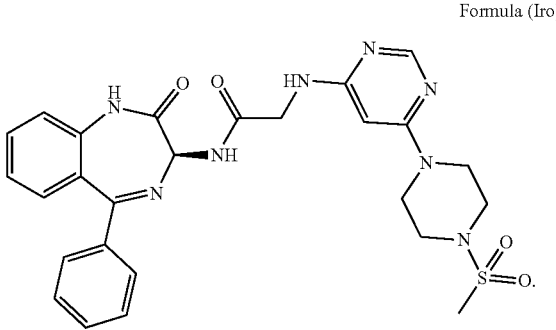

13. A method of treating or ameliorating a microbial infection, the method comprising administering, to a subject in need of such treatment, a therapeutically effective amount of a compound of formula (I), as defined by claim 1, or a pharmaceutically acceptable salt, solvate, tautomeric form or polymorphic form thereof.

14. The method according to claim 13, wherein the microbial infection comprises a viral infection.

15. A pharmaceutical composition comprising a compound in accordance with claim 1, or a pharmaceutically acceptable salt, solvate, tautomeric form or polymorphic form thereof, and a pharmaceutically acceptable vehicle.

16. A method of manufacturing a compound in accordance with claim 1, the method comprising contacting a compound of formula (II), or a salt or solvate thereof:

Formula (II)

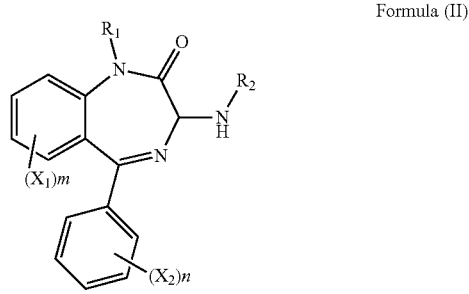

with a compound of formula (III), or a salt or solvate thereof:

Formula (III)

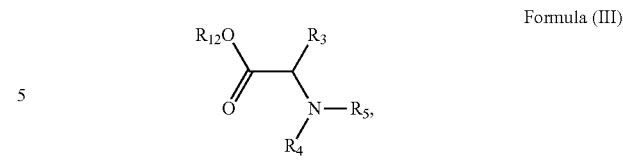

wherein $R_1$ is H;

$R_2$ is H;

$R_3$ is a side chain of a naturally occurring amino acid; and $R_4$ is H; or $R_3$ and $R_4$, together with the atoms to which they are attached, combine to form a five-membered heterocyclic ring;

$R_5$ is an aromatic six membered ring optionally substituted with one or more substituents, wherein the or each substituent is independently a $C_{1-5}$ straight or branched alkyl or alkenyl, a halogen, $SR_6$, $SO_2R_6$, $OR_6$, or $NR_6R_7$;

m is 0, 1, 2, 3 or 4;

n is 0, 1, 2, 3, 4 or 5;

the or each $X_1$ is independently selected from a $C_{1-5}$ straight or branched alkyl or alkenyl, a halogen, $SR_6$, $SO_2R_6$, $OR_6$ or $NR_6R_7$;

the or each $X_2$ is independently selected from a C1-5 straight or branched alkyl or alkenyl, chlorine, bromine, $SR_6$, $SO_2R_6$, $OR_6$ or $NR_6R_7$;

the or each $R_6$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

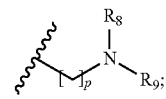

the or each $R_7$ is independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, $C_{2-4}$ dialkylaminoalkyl and

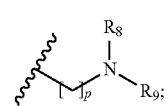

and/or $R_6$ and $R_7$ together with the nitrogen atom to which they are attached independently form a 3-7 membered ring;

p is 1, 2, 3, 4 or 5;

$R_8$ and $R_9$ together with the nitrogen atom to which they are attached independently form a 3-7 membered ring; and $R_{12}$ is H or a $C_{1-5}$ straight or branched alkyl or alkenyl.

17. The method according to claim 16, wherein $R_{12}$ is hydrogen.

18. The compound of claim 8, wherein and the or each halogen is a fluorine.

19. The compound of claim 10, wherein $X_3$ is a halogen or $SO_2R_6$.

20. The compound of claim 10, wherein the or each $X_2$ is independently a Cis straight or branched alkyl or alkenyl, $SR_6$, $SO_2R_6$, $OR_6$ or $NR_6R_7$.

21. The method according to claim 14, wherein the viral infection is Respiratory Syncytial Virus (RSV).

* * * * *

UNITED STATES PATENT AND TRADEMARK OFFICE
CERTIFICATE OF CORRECTION

PATENT NO. : 11,247,973 B2  
APPLICATION NO. : 16/323496  
DATED : February 15, 2022  
INVENTOR(S) : Stuart Cockerill Page 1 of 1

It is certified that error appears in the above-identified patent and that said Letters Patent is hereby corrected as shown below:

In the Specification

In Column 63, Line 41, please replace "trifluoropridin" with --- trifluoropyridin ---;

In Column 64, Line 41, please replace "water (is ml)" with --- water (15 ml) ---;

In Column 65, Line 9, please replace "(2×5 ml)" with --- (2×50 ml) ---;

In Column 71, Line 66, please replace "Cis" with --- C1-s ---; and

In Column 79, Line 2, please replace "Cis" with --- C1-s ---.

Signed and Sealed this  
Ninth Day of August, 2022

Katherine Kelly Vidal  
*Director of the United States Patent and Trademark Office*